(12) United States Patent
Han et al.

(10) Patent No.: US 12,038,431 B2
(45) Date of Patent: Jul. 16, 2024

(54) HIGH-THROUGHPUT SCREENING SYSTEM FOR IDENTIFICATION OF NOVEL DRUGS AND DRUG TARGETS

(71) Applicant: MEDIC LIFE SCIENCES INC., Mountain View, CA (US)

(72) Inventors: Kyuho Han, Palo Alto, CA (US); Hong-Pyo Lee, Palo Alto, CA (US)

(73) Assignee: MEDIC Life Sciences Inc., Mountain View, CA (US)

( * ) Notice: Subject to any disclaimer, the term of this patent is extended or adjusted under 35 U.S.C. 154(b) by 0 days.

(21) Appl. No.: 18/054,595

(22) Filed: Nov. 11, 2022

(65) Prior Publication Data

US 2023/0083853 A1 Mar. 16, 2023

Related U.S. Application Data

(62) Division of application No. 17/811,290, filed on Jul. 7, 2022, now Pat. No. 11,802,866.

(60) Provisional application No. 63/219,665, filed on Jul. 8, 2021.

(51) Int. Cl.
| | |
|---|---|
| *C07K 19/00* | (2006.01) |
| *C12N 15/10* | (2006.01) |
| *G01N 33/50* | (2006.01) |

(52) U.S. Cl.
CPC ......... *G01N 33/5008* (2013.01); *C07K 19/00* (2013.01); *C12N 15/1037* (2013.01); *G01N 33/5011* (2013.01); *G01N 33/502* (2013.01); *C07K 2319/03* (2013.01); *C07K 2319/035* (2013.01); *G01N 2500/04* (2013.01)

(58) Field of Classification Search
CPC ................ C07K 19/00; C07K 2319/03; C07K 2319/035; C12N 15/1037; G01N 33/5008; G01N 33/5011; G01N 33/502; G01N 2500/04

See application file for complete search history.

(56) References Cited

U.S. PATENT DOCUMENTS

2019/0345491 A1* 11/2019 Zhao .................. C07K 14/4705

FOREIGN PATENT DOCUMENTS

| WO | WO 2015/128509 A1 | 9/2015 |
| WO | WO 2016/138491 A1 | 9/2016 |
| WO | WO 2019/191114 A1 | 10/2019 |
| WO | WO 2019/222284 A1 | 11/2019 |
| WO | WO-2021226543 A2 * | 11/2021 |

OTHER PUBLICATIONS

Liao et al. (Gene Therapy, 2000, 7:339-347) (Year: 2000).*
Hu et al. (Frontiers in Immunology, 2020, 11:1770, doi: 10.3389/fmmu.2020.01770) (Year: 2020).*

(Continued)

*Primary Examiner* — Jeremy C Flinders
(74) *Attorney, Agent, or Firm* — Fenwick & West LLP; Hayan Yoon; Filip Vanevski

(57) ABSTRACT

The present disclosure provides a high-throughput screening system and method for identification of novel drugs and drug targets. The method enables large-scale analysis of interactions between allogeneic pairs of target cells and immune cells by using an immune-bridge protein, library of guide RNA, and/or 3D tumor model.

8 Claims, 16 Drawing Sheets
(16 of 16 Drawing Sheet(s) Filed in Color)
Specification includes a Sequence Listing.

(56) References Cited

OTHER PUBLICATIONS

Chaudhuri, O. et al., "Hydrogels with tunable stress relaxation regulate stem cell fate and activity," Nature Materials 15(3), Nov. 30, 2015, pp. 326-334.

Han, K. et al., "CRISPR screens in cancer spheroids identify 3D growth-specific vulnerabilities," Nature 580(7801), Mar. 11, 2020, pp. 136-141.

Han, K. et al., "Synergistic drug combinations for cancer identified in a CRISPR screen for pairwise genetic interactions," Nature Biotechnology 35(5), Mar. 20, 2017, pp. 463-474.

Kameni, F.N. et al., "Anti-NKp46 CAR T Cell to Target NK Cell Malignancies," Molecular Therapy, vol. 28, Issue 4, Supplement 1, Apr. 28, 2020, pp. 146-147.

Liao, K-W. et al., "Design of Transgenes for Efficient Expression of Active Chimeric Proteins on Mammalian Cells," Biotechnology and Bioengineering, vol. 73, No. 4, Mar. 27, 2001, pp. 313-323.

Lee, H-P. et al., "Mechanical confinement regulates cartilage matrix formation by chondrocytes," Nature Materials 16(12), Oct. 2, 2017, pp. 1243-1251.

Lee, H-P. et al., "vol. expansion and TRPV4 activation regulate stem cell fate in three-dimensional microenvironments," Nature Communications, vol. 10, Jan. 31, 2019, pp. 1-13.

PCT International Search Report and Written Opinion, PCT Application No. PCT/US2022/073510, Jan. 23, 2023, 31 pages.

PCT Invitation to Pay Additional Fees, PCT Application No. PCT/US2022/073510, Nov. 25, 2022, 22 pages.

Wang, C. et al., "Imaging-based pooled CRISPR screening reveals regulators of lncRNA localization," PNAS, vol. 116, No. 22, May 28, 2019, pp. 10842-10851.

Dufva, O. et al. "Integrated drug profiling and CRISPR screening identify essential pathways for CAR T-cell cytotoxicity," Blood, *The Journal of the American Society of Hematology*, vol. 135, No. 9, Feb. 27, 2020, pp. 597-609.

United States Office Action, U.S. Appl. No. 17/811,290, filed Aug. 11, 2023, 13 pages.

United States Office Action, U.S. Appl. No. 17/811,290, filed May 23, 2023, 13 pages.

\* cited by examiner i. Traditional approach ii. MEDiC's approach

SEQUENCE LISTING

```
Sequence total quantity: 2
SEQ ID NO: 1            moltype = AA  length = 23
FEATURE                 Location/Qualifiers
source                  1..23
                        mol_type = protein
                        organism = synthetic construct
SEQUENCE: 1
VLFGAGFGAV ITVVVIVVII KCF                                                  23

SEQ ID NO: 2            moltype = AA  length = 35
FEATURE                 Location/Qualifiers
source                  1..35
                        mol_type = protein
                        organism = synthetic construct
SEQUENCE: 2
CKHRSCFRRN EASRETNNSL TFGPEEALAE QTVFL                                     35
```

HIGH-THROUGHPUT SCREENING SYSTEM FOR IDENTIFICATION OF NOVEL DRUGS AND DRUG TARGETS

1. CROSS REFERENCE TO RELATED APPLICATIONS

This application is a divisional of U.S. application Ser. No. 17/811,290 filed on Jul. 7, 2022, which claims the benefit of and priority to U.S. Provisional Application No. 63/219,665, filed on Jul. 8, 2021, each of which is incorporated herein by reference in its entirety for all purposes.

SEQUENCE LISTING

The instant application contains a Sequence Listing which has been submitted via Patent Center and is hereby incorporated by reference in its entirety. Said XML copy, created on Nov. 10, 2022, is named 54232sequencelisting.xml, and is 2,913 bytes in size.

2. BACKGROUND OF THE INVENTION

Immunotherapy is a powerful therapeutic approach for treatment of cancer. However, its application has been limited because checkpoint blockade immunotherapies do not work for many patients, particularly patients with solid tumors. Several intrinsic and extrinsic factors have been suggested to contribute to the resistance, including altered signaling pathways, immuno-suppressive tumor microenvironment, and poor infiltration of effective T cells to the tumor microenvironment. Researchers have tried to overcome the limitations, by studying mechanisms of drug response and clinical outcome in cancer patients, and by developing novel therapeutics for the patients having no or low response to existing immunotherapies. However, research in the field has been difficult because cell-based assay systems traditionally used for screening drug response and immune recognition are not universally applicable to various cancer and/or immune effector cell types. The traditional high-throughput screening systems are not optimal for large scale studies because they require immune cells and cancer models prepared from genetically identical, syngeneic mouse models. Furthermore, use of two-dimensional (2D) cell cultures failed to recapitulate tumor microenvironment, because 2D cell cultures induce disturbance of interactions between the cellular and extracellular environments and changes in cell morphology, polarity, and method of division.

Accordingly, there is a need for a better high throughput assay system to identify novel drug targets and develop more effective drugs.

3. SUMMARY OF THE INVENTION

The present disclosure provides cell-based high throughput screening systems for identification of novel drug targets and development of drugs for treatment of cancer or immune disorders.

The assay systems provided herein leverages 1) an immune-bridge protein comprising an antigen binding protein (e.g., single-chain variable fragments (scFv)) that can recruit and activate specific immune effector cells such as T cells and NK cells, and/or 2) high-throughput screening platforms using an RNA-guided nuclease (e.g., CRISPR).

The immune-bridge protein is an artificial protein that contains an scFV molecule that binds to an immune cell marker, such as CD3 on T cells or NKp46 on NK cells. Thus, the immune-bridge protein can specifically interact with immune effector cells. Applicant demonstrated that the immune-bridge protein expressed on cancer cells can recruit and activate immune effector cells, thereby leading to targeted killing of the cancer cells. The interaction between the immune-bridge protein and the immune cell marker allows recapitulation of specific and selective interactions between immune cells and cancer cells regardless of their sources. Accordingly, the immune-bridge protein expressed on cancer cells can be used to induce activation of immune effector cells against the cancer cells and analyze response of the cancer cells to the activated immune effector cells. The system can be used for high-throughput screening of drugs and/or genes that are involved in modulation of the response of the cancer cells to the activated immune effector cells, thereby involved with the immuno-oncology functions.

Applicant further combined the high throughput screening systems with a 3D tumor culture system using microcapsule-based compartmentalization technology. It allowed 3D growth of multiple cancer samples in a single tissue-culture container without crosstalk with other samples. Barcoding of the tumor samples further allows multiplexing and demultiplexing of multiple samples while allowing tracing of their identity. Previously, 3D cultures in a large scale were technically challenging, laborious and time-consuming. Thus, use of 3D culture in the high-throughput screening has been limited although it is expected to provide better recapitulation of patients' tumors than traditional 2D cancer models. The present disclosure adopts microcapsule-based 3D culture system that overcomes the limitations and enables simultaneous culture and analysis of multiplexed tumor samples, where each cancer sample is barcoded.

In the 3D culture system, cancer cells are encapsulated in microcapsules, where they can grow into spherical tumors. Several cancer samples encapsulated in separate populations of microcapsules can be pooled and cultured in a single tissue-culture container. After the culture, the tumor samples can be collected from the microcapsules and their genomic DNAs can be extracted and analyzed to characterize cancer cells remaining in the culture, for example, by sequencing the DNA barcodes, sg RNA sequences in case of CRISPR system, etc. This system fundamentally solves the scalability limitations of the traditional systems and enables drug tests and CRISPR functional genomics in 3D tumors by greatly simplifying the time-consuming and laborious process.

Accordingly, the present disclosure provides an immune-bridge protein comprising from N terminus to C terminus: a. a scFv against an immune cell marker, b. a transmembrane domain, c. a cytoplasmic domain, and d. a reporter domain, optionally wherein the reporter domain is a fluorescent protein.

In some embodiments, the immune cell marker is a cell surface protein of a T cell or NK cell. In some embodiments, the immune cell marker is CD3. In some embodiments, the immune cell marker is NKp46. In some embodiments, the transmembrane domain is a transmembrane domain of B7. In some embodiments, the cytoplasmic domain is a cytoplasmic domain of B7.

In some embodiments, the immune-bridge protein further comprises an epitope for immunostaining in the intracellular or extracellular portion of the immune-bridge protein, optionally wherein the epitope is selected from HA epitope and V5 epitope. In some embodiments, the immune-bridge protein further comprises a signal peptide at the N-terminal end of the immune-bridge protein, optionally an H7 signal peptide. In some embodiments, the immune-bridge protein further comprises a hinge-CH2-CH3 region of human IgG1 in the extracellular portion of the immune-bridge protein.

The present disclosure also provides an immune-bridge polynucleotide encoding the immune-bridge protein described herein. It also provides an immune-bridge vector comprising a polynucleotide encoding the immune-bridge protein described herein. In some embodiments, the vector is a viral vector or a plasmid. In some embodiments, the vector is a lentiviral vector.

In one aspect, the present disclosure provides a targeting library comprising a plurality of targeting-library constructs, wherein each of the targeting-library constructs comprises a sgRNA-coding sequence encoding a sgRNA targeting one of a plurality of genomic target sites. In some embodiments, each targeting-library construct further comprises a barcode sequence.

In some embodiments, the plurality of targeting-library constructs comprise sgRNA-coding sequences encoding sgRNAs collectively targeting more than 10,000 sites in the human genome. In some embodiments, the plurality of targeting-library constructs comprise sgRNA-coding sequences encoding sgRNAs collectively targeting more than 15,000 sites in the human genome. In some embodiments, the plurality of targeting-library constructs comprise sgRNA-coding sequences encoding sgRNAs collectively targeting more than 20,000 sites in the human genome. In some embodiments, the plurality of targeting-library constructs comprise sgRNA-coding sequences encoding sgRNAs collectively targeting more than 50,000 sites in the human genome. In some embodiments, the plurality of targeting-library constructs comprise sgRNA-coding sequences encoding sgRNAs collectively targeting more than 100,000 sites in the human genome.

In some embodiments, each targeting-library construct comprises a unique pair of the sgRNA-coding sequence and the barcode sequence.

In some embodiments, each targeting-library construct further comprises a coding sequence of an endonuclease. In some embodiments, the endonuclease is a clustered regularly interspaced short palindromic repeats (CRISPR) associated protein, a zinc-finger nuclease (ZFN), a transcription activator-like effector nuclease (TALEN), or a meganuclease (MN).

In some embodiments, the endonuclease is CAS9. In some embodiments, each targeting-library construct is a viral vector or a plasmid. In some embodiments, each targeting-library construct is a lentiviral vector.

In another aspect, the present disclosure provides a population of cells, wherein at least a plurality of cells in the population comprises a targeting-library construct described herein, wherein the population of cells collectively comprises multiple types of targeting-library constructs. In some embodiments, the population of cells further comprise the immune-bridge protein of the present disclosure. In some embodiments, the population of cells comprise the immune-bridge polynucleotide or the immune-bridge vector of the present disclosure.

In some embodiments, the cells are cancer cells. In some embodiments, the cells are one or more cancer cell lines. In some embodiments, the population of cells comprise multiple cell lines, wherein each cell line comprises a unique cell line-specific barcode on the targeting-library construct or immune-bridge polynucleotide. In some embodiments, the cells are primary cancer cells. In some embodiments, the cells are primary cancer cells from one or more cancer patients. In some embodiments, the population of cells comprise primary cancer cells from multiple cancer patients, wherein cells from a single cancer patient comprises a unique patient-specific barcode on the targeting-library construct or immune-bridge polynucleotide. In some embodiments, the cells are solid tumor cells.

In some embodiments, the cells have been transfected with the immune-bridge polynucleotide, the immune-bridge vector, or the targeting library of the present disclosure. In some embodiments, the cells have been transfected with the immune-bridge polynucleotide or the immune-bridge vector, and the targeting library provided herein.

In some embodiments, the population of cells further comprise a marker protein encoded the targeting-library construct or immune-bridge polynucleotide. In some embodiments, the marker protein is luciferase. In some embodiments, the population of cells further comprise an exogenous endonuclease. In some embodiments, the endonuclease is a clustered regularly interspaced short palindromic repeats (CRISPR) associated protein, a zinc-finger nuclease (ZFN), a transcription activator-like effector nuclease (TALEN), or a meganuclease (MN). In some embodiments, the endonuclease is CAS9. In some embodiments, at least a plurality of cells in the population comprises the immune-bridge protein described herein.

One aspect of the present disclosure provides a pool of microcapsules encapsulating the population of cells of the present disclosure. In some embodiments, each of the microcapsules encapsulates a subset of the population of cells comprising a same barcode sequence. In some embodiments, the same barcode sequence is a sequence of a cell line-specific barcode or a patient specific barcode. In some embodiments, each of the microcapsules encapsulates a subset of the population of cells obtained from a same subject. In some embodiments, each of the microcapsules encapsulates a subset of the population of cells obtained from a same cancer patient. In some embodiments, each of the microcapsules encapsulates a subset of the population of cells obtained from a single cell line.

In some embodiments, each of the microcapsules encapsulates a subset of the population of cells comprising two or more different barcode sequences. In some embodiments, the two or more different barcode sequences are sequences of cell line-specific barcodes or patient specific barcodes. In some embodiments, each of the microcapsules encapsulates a subset of the population of cells obtained from two or more subjects. In some embodiments, each of the microcapsules encapsulates a subset of the population of cells obtained from two or more cancer patients. In some embodiments, each of the microcapsules encapsulates a subset of the population of cells obtained from two or more cell lines.

In some embodiments, the pool of microcapsules, further encapsulate immune cells. In some embodiments, the immune cells comprise T cells. In some embodiments, the immune cells comprise NK cells. In some embodiments, the immune cells comprise dendritic cells. In some embodiments, the immune cells comprise macrophage. In some embodiments, the immune cells comprise peripheral blood mononuclear cells (PBMCs).

In some embodiments, the pool of microcapsules are incubated in a culture medium. In some embodiments, the population of cells form a 3D tumor organoid.

In another aspect, the present disclosure provides a method of high-throughput screening, comprising the steps of: a. culturing the population of cells or incubating the pool of microcapsules of the present disclosure; and b. analyzing cells obtained from the culture. In some embodiments, the step of analyzing comprises sequencing targeting-library constructs of cells obtained from the culture. In some embodiments, the step of analyzing comprises sequencing barcode sequences in the targeting-library constructs. In some embodiments, the step of analyzing comprises sequencing the coding sequence of sgRNA in the targeting-library constructs. In some embodiments, the method further comprises the step of identifying a genomic site associated with survival or death of cells in the culture condition.

In some embodiments, the population of cells are cultured in the presence of immune cells. In some embodiments, the method further comprises the step of culturing a different population of cells in the absence of immune cells. In some embodiments, the method further comprises the step of identifying an immune-oncology target by identifying a genomic site associated with survival or death of cells in the culture condition. In some embodiments, the method further comprises the step of comparing cells obtained from the culture in the presence of immune cells and cells from the culture in the absence of immune cells.

In some embodiments, the method further comprises the step of identifying an immune-oncology target by identifying a genomic site associated with survival or death of cells in one or more culture conditions.

In some embodiments, the immune cells comprise T cells. In some embodiments, the immune cells comprise NK cells. In some embodiments, the immune cells comprise dendritic cells. In some embodiments, the immune cells comprise macrophage. In some embodiments, the immune cells comprise peripheral blood mononuclear cells (PBMCs).

In some embodiments, the population of cells are cultured in the presence of one or more drugs. In some embodiments, the population of cells are cultured further in the presence of immune cells. In some embodiments, the method further comprises the step of culturing a different population of cells in the absence of the one or more drugs. In some embodiments, the method further comprises the step of comparing cells obtained from the culture in the presence of one or more drugs and cells obtained from the culture in the absence of one or more drugs. In some embodiments, the method further comprises the step of identifying an effective drug by identifying a drug associated with survival or death of cells in one or more culture conditions. In some embodiments, the method further comprises the step of identifying a drug target by identifying a genomic site associated with survival or death of cells in one or more culture conditions. In some embodiments, the method further comprises the step of culturing a different population of cells in the absence of immune cells. In some embodiments, the method further comprises the step of comparing cells obtained from the culture in the presence of immune cells and cells obtained from the culture in the absence of immune cells. In some embodiments, the method further comprises the step of identifying an effective drug by identifying a drug associated with survival or death of cells in one or more culture conditions. In some embodiments, the method further comprises the step of identifying a drug target by identifying a genomic site associated with survival or death of cells in one or more culture conditions.

In some embodiments, the step of culturing is performed in a culture dish or multi-well plate. In some embodiments, the step of culturing is performed in a plurality of microcapsules. In some embodiments, the step of culturing is performed in a 3D tumor organoid.

In yet another aspect, the present disclosure provides a kit for high throughput screening comprising: a. the immune-bridge polynucleotide, or the immune-bridge vector, and b. the targeting library provided herein. In some embodiments, the kit further comprises a nuclease polynucleotide encoding an exogenous nuclease. In some embodiments, the exogenous nuclease is selected from the group consisting of a clustered regularly interspaced short palindromic repeats (CRISPR) associated protein, a zinc-finger nuclease (ZFN), a transcription activator-like effector nuclease (TALEN), and a meganuclease (MN). In some embodiments, the exogenous nuclease is CAS9. In some embodiments, the kit further comprises a marker polynucleotide encoding a marker protein. In some embodiments, the marker protein is luciferase. In some embodiments, the nuclease polynucleotide or the marker polynucleotide is a viral vector, optionally a lentiviral vector.

4. BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

These and other features, aspects, and advantages of the present invention will become better understood with regard to the following description, and accompanying drawings, where:

FIG. 1 provides the structure of constructs for generating immune-bridge proteins (pMED178, pMED179, pMED200, and pMED201) as described in Example 1.

FIGS. 2A and 2B compare a traditional high throughput system for identifying immune modulators using OVA or HA antigens (FIG. 2A) and a novel system using an immune-bridge protein (FIG. 2B).

Figure 6B:
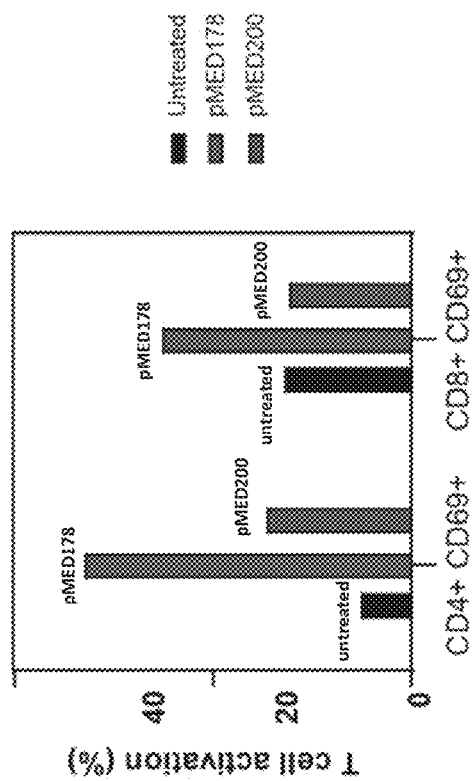
Figure 6A:
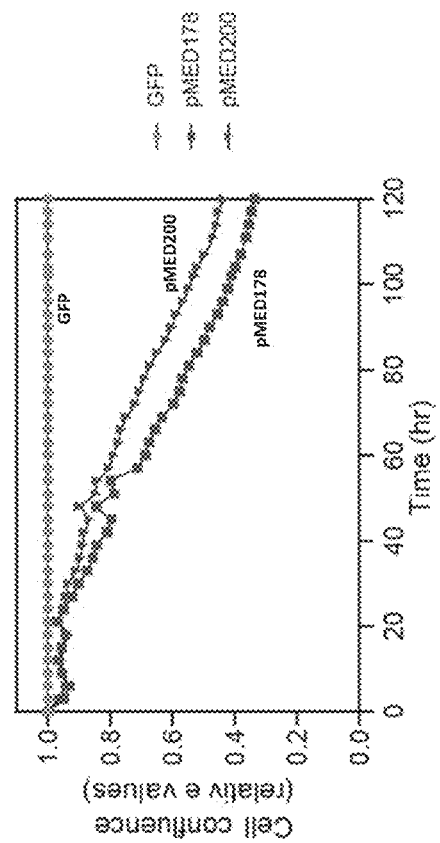

FIG. 6A provides relative growth of cancer cells expressing an immune-bridge protein (pMED178 or pMED200) in the presence of human naïve T cells compared to control GFP cells. FIG. 6B shows levels of T cell activation (%) measured by an early T cell activation marker, CD69, by cancer cells expression an immune-bridge protein (pMED178 or pMED200).

Figure 7:
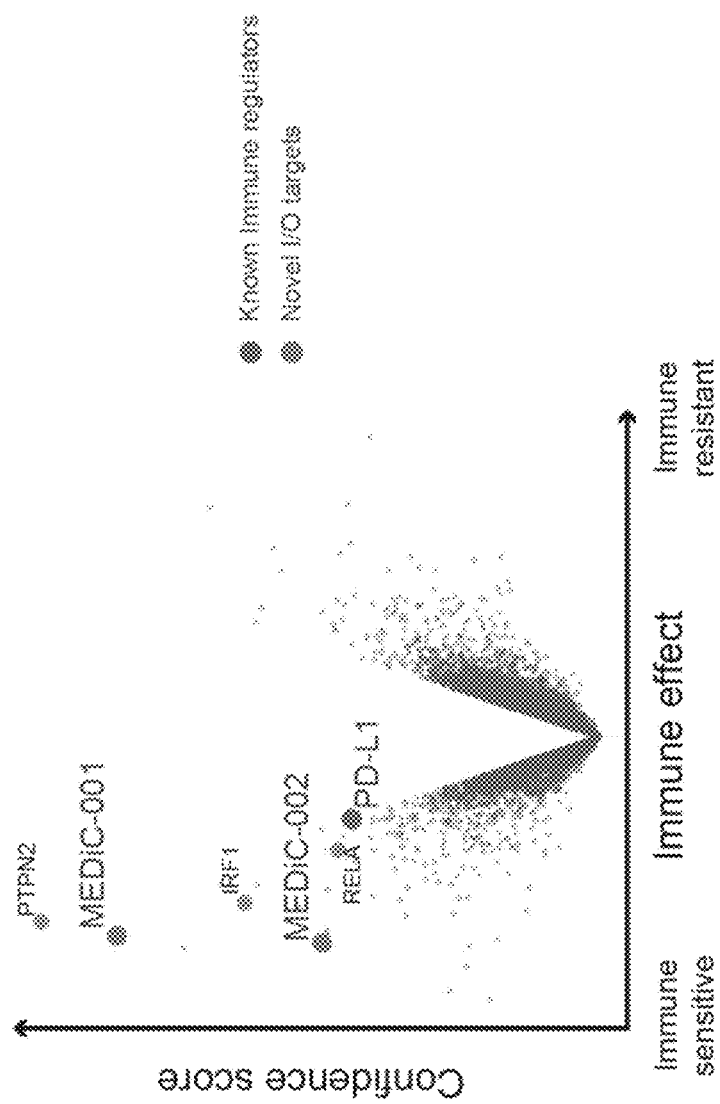

FIG. 7 is a volcano plot of genome-scale CRISPR screening data described in Example 2.

Figure 8:
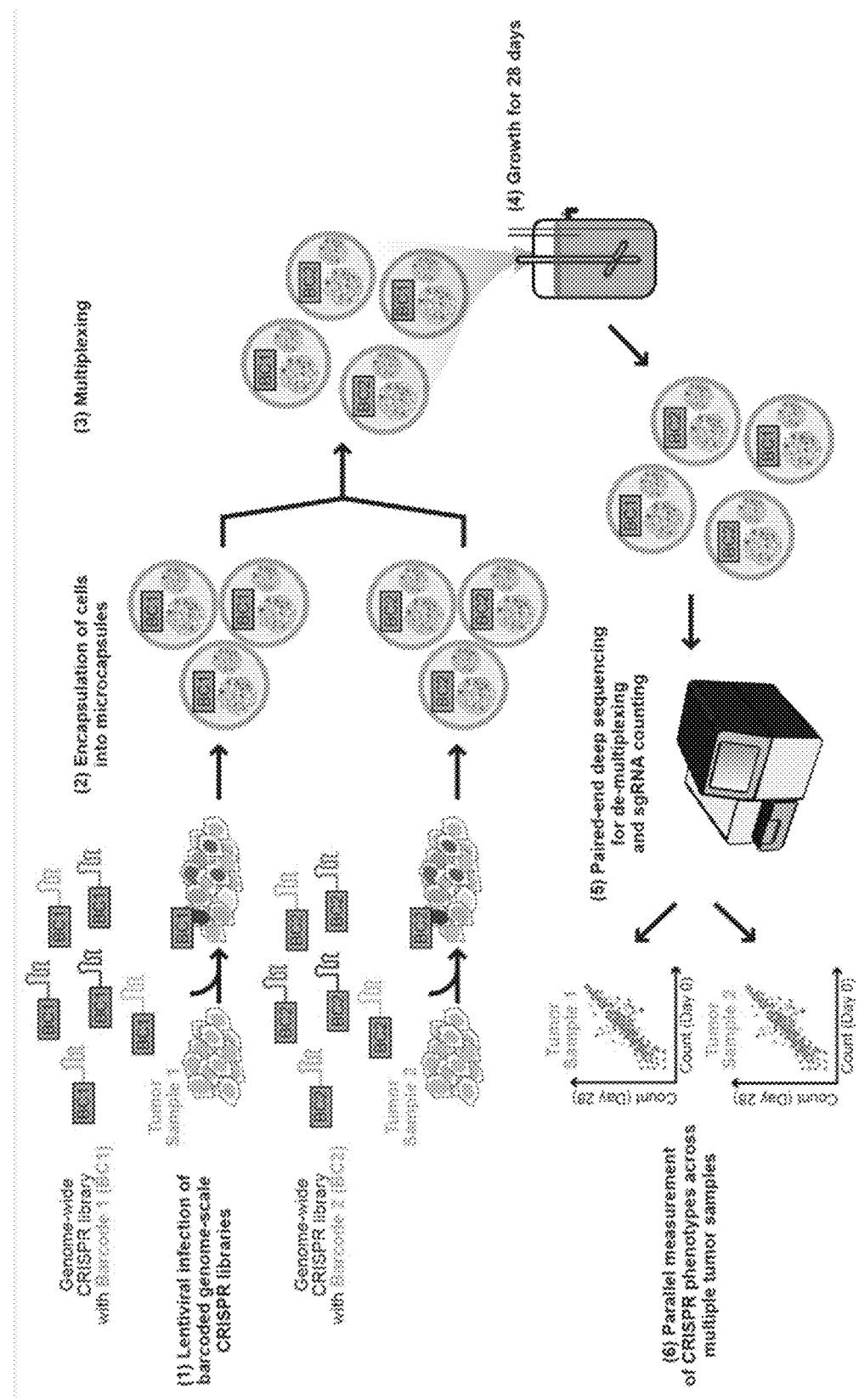

FIG. 8 provides a schematic of multiplexed CRISPR functional genomics in 3D tumor models as described in Example 6.

Figures 9A, 9B:
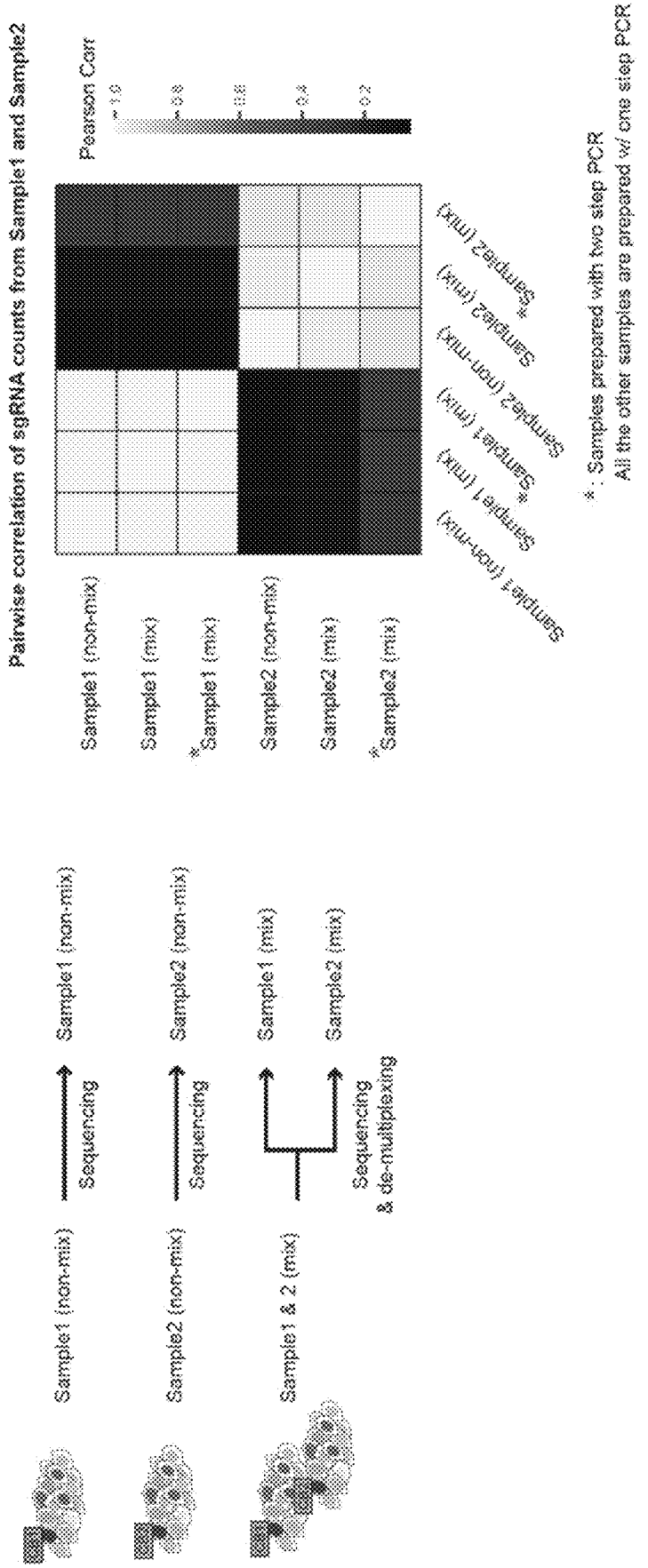

FIG. 9A outlines an experimental procedure performed to compare sgRNA counts between individually cultured cancer (non-mix) samples and multiplexed cancer samples (mix). FIG. 9B is a heatmap showing pairwise correlation of sgRNA counts between mixed samples and non-mixed samples.

Figure 10B:
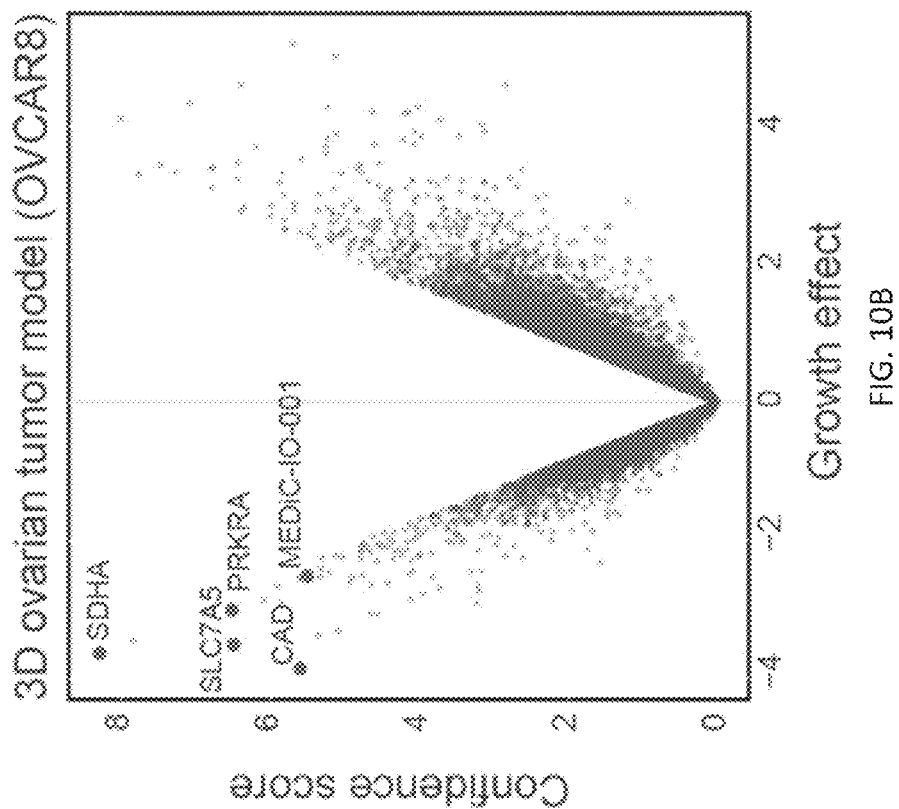
Figure 10A:
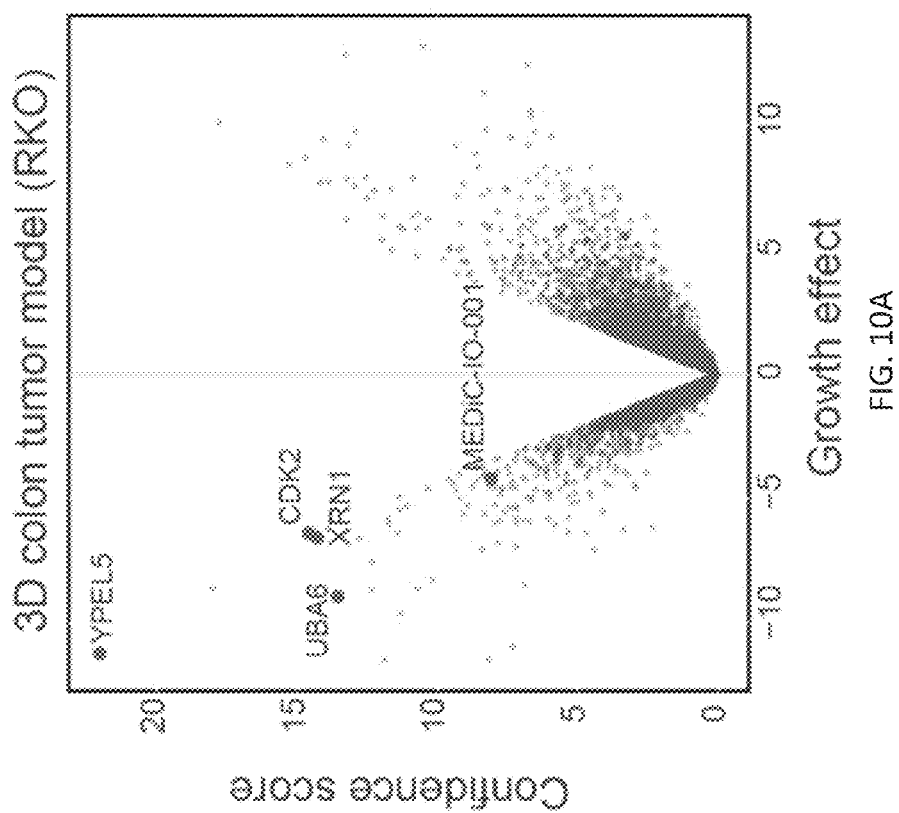

FIG. 10A is a volcano plot of genome-scale CRISPR screening data from 3D colon tumor model (RKO) described in Example 7. FIG. 10B is a volcano plot of genome-scale CRISPR screening data from 3D ovarian tumor model (OVCAR8) as described in Example 7.

Figure 11B:
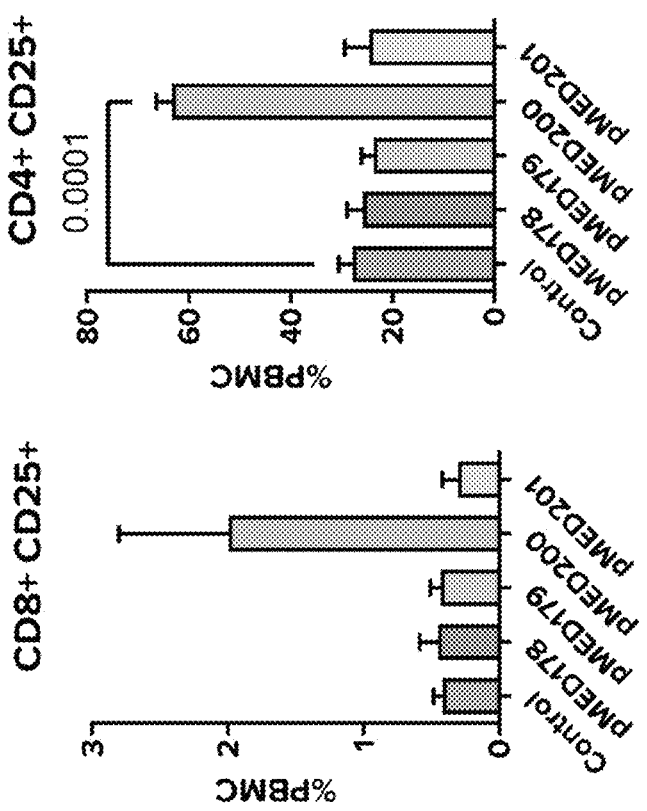
Figure 11A:
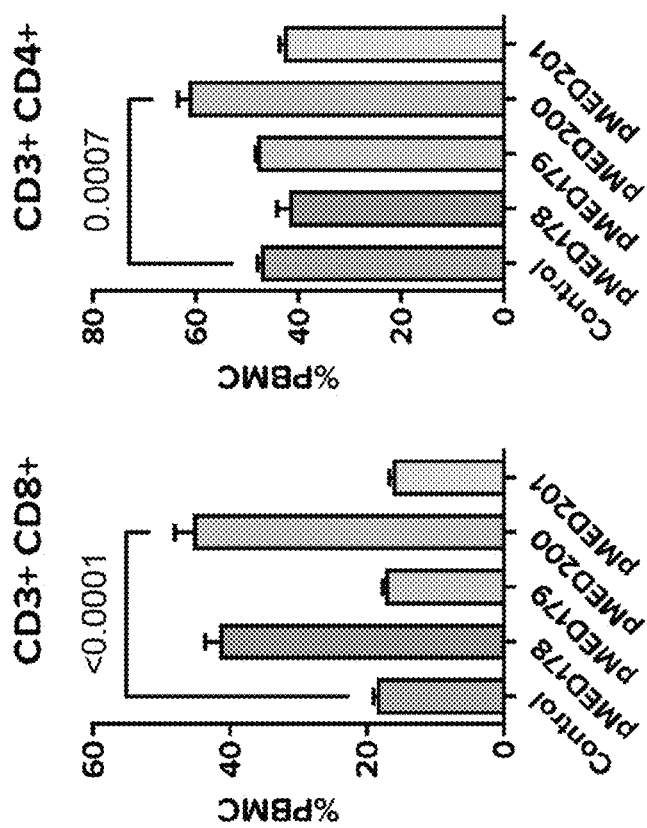

FIG. 11A shows percentage of CD3+/CD8+ and CD3+/CD4+ cells in PBMCs exposed to cancer cells with indicated immune-bridges as measured by cell analyzer (Bio-Rad ZE5). FIG. 11B shows percentage of CD8+/CD25+(CD25+: T cell activation marker) and CD4+/CD25+ cells in PBMCs exposed to cancer cells with the indicated immune-bridges as measured by cell analyzer (Bio-Rad ZE5).

Figure 12:
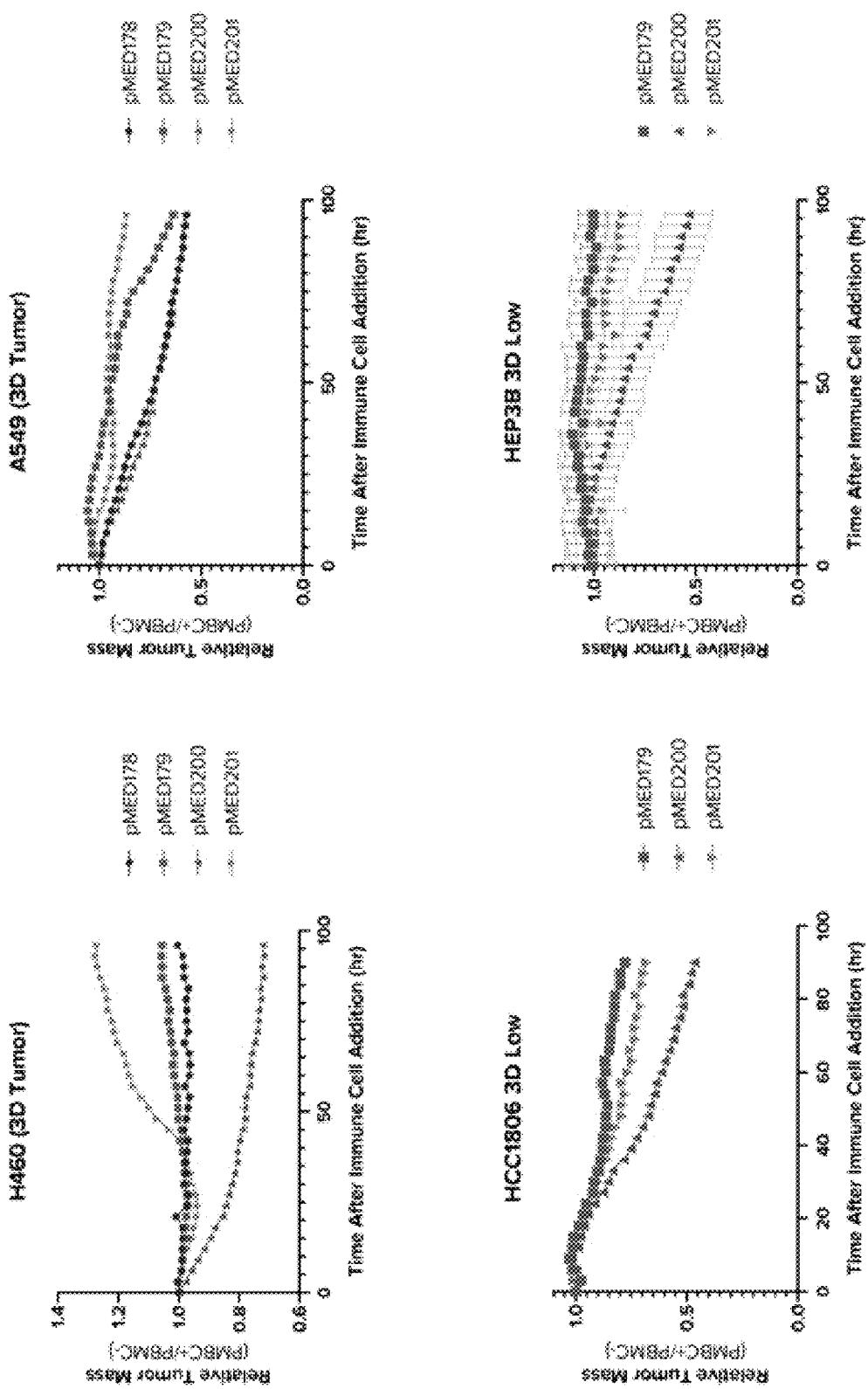
Figure 12:
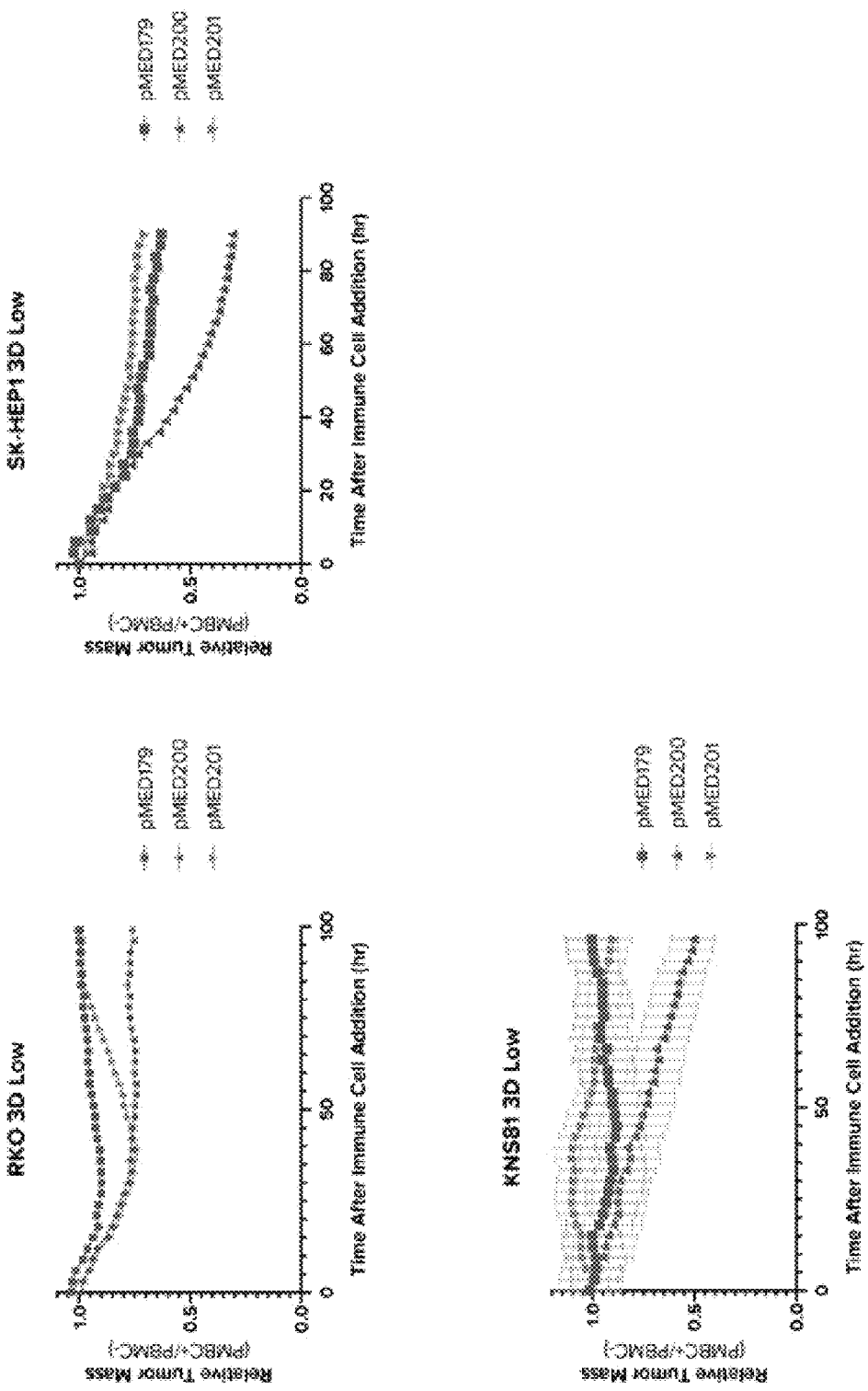

FIG. 12 provides the tumor mass measured by GFP signals of immune-bridges (pMED178, pMED179, pMED200 and pMED201) in Incucyte S3 (Sartorius), a live-cell time-lapse microscopy system. Relative tumor mass between PBMC+ and PBMC− samples was plotted after PBMCs were added. pMED200 consistently induced substantial tumor cell death whereas pMED178 was inconsistent. pMED179 and pMED201 (negative controls) do not induce significant tumor cell death with human PBMCs.

Figure 13:
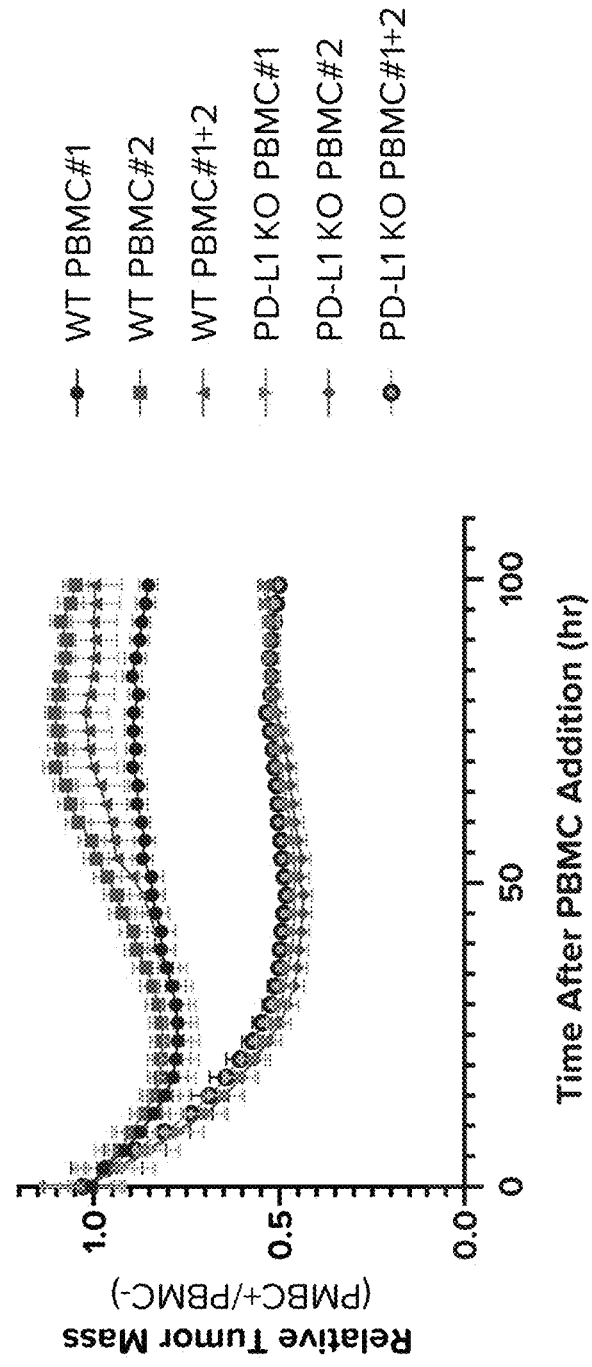

FIG. 13 shows that wild type and PD-L1 KO cells expressing pMED200 showed differential sensitivities against PBMC. hPBMCs were added to Wild type and PD-L1 KO triple negative breast cancer (TNBC) cell lines and relative tumor mass was monitored over time in Incucyte S3 by GFP marker expressed in the tumors. Three different PBMC combinations (PBMC #1, #2, and #1+2) were used. This tumor-immune co-culture functional assay clearly proved that pMED200 can be used to recapitulate specific interactions between human immune cells and tumor cells with various genetic contexts.

Figures 14A, 14B:
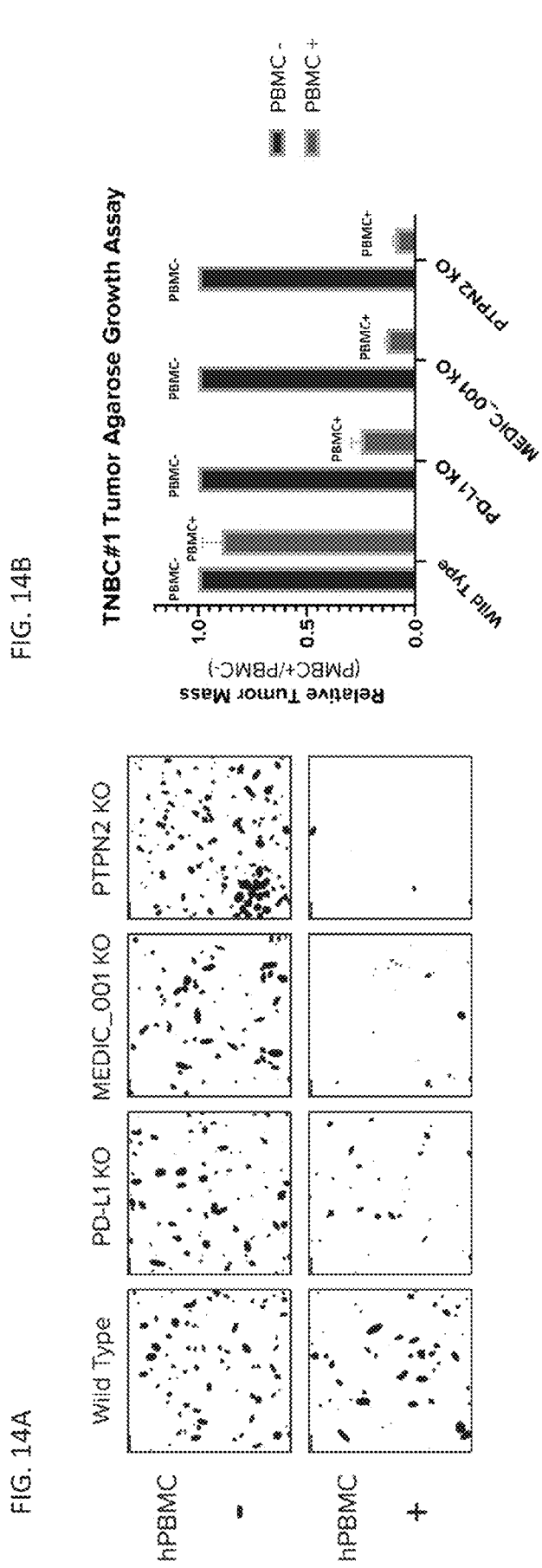

FIG. 14A provides images of tumor cell cultures with GFP signals. The cultures include TNBC cells (TNBC #1) with the indicated gene knockouts seeded in agarose gel with and without hPBMCs. PD-L1, PTPN2 KO as well as MEDIC_001 KO showed greater tumor reductions by hPBMCs than the wild type.

FIG. 14B is a graph summarizing the relative tumor mass between PBCM+ and PBMC− samples measured in the culture provided in FIG. 14A. It provides data for wild type, PD-L1 KO, MEDIC_001 KO, and PTPN2 KO TNBC #1 tumors.

Figure 15B:
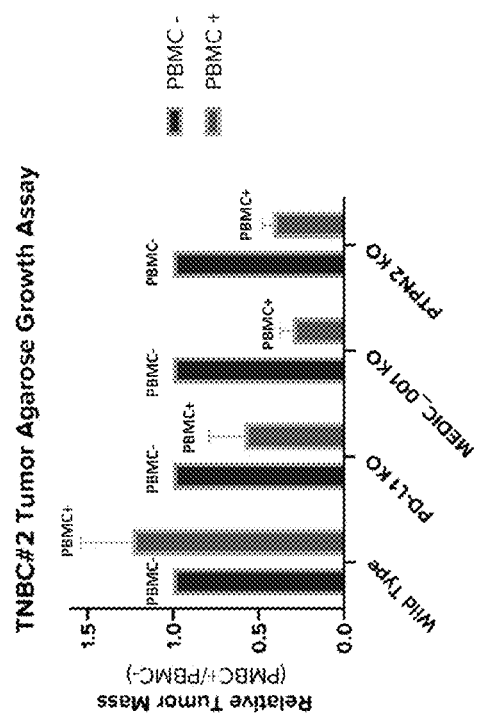
Figure 15A:
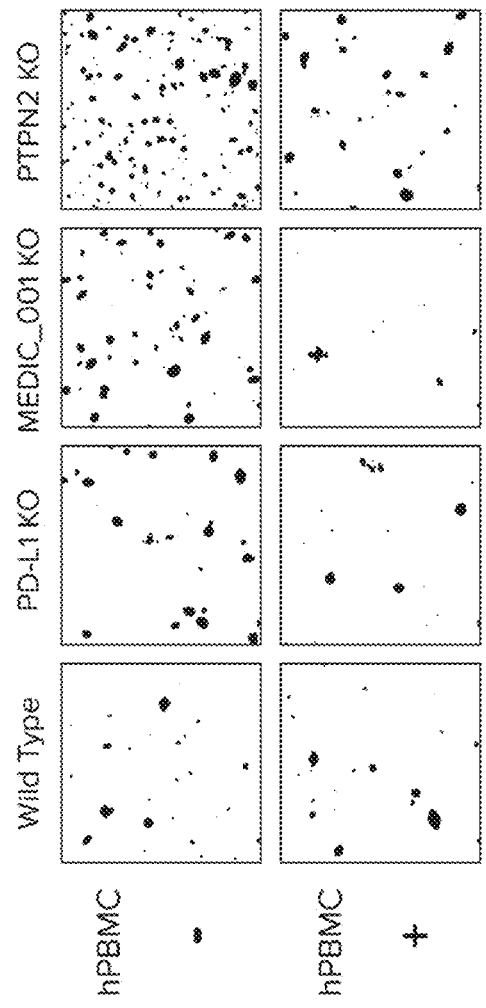

FIG. 15A provides images of tumor cell cultures with GFP signals. The cultures include TNBC cells (TNBC #2) with the indicated gene knockouts seeded in agarose gel with and without hPBMCs. PD-L1, PTPN2 KO as well as MEDIC_001 KO showed greater tumor reductions by hPBMCs than the wild type.

FIG. 15B is a graph summarizing the relative tumor mass between PBCM+ and PBMC− samples measured in the culture provided in FIG. 15A. It provides data for wild type, PD-L1 KO, MEDIC_001 KO, and PTPN2 KO TNBC #2 tumors.

5. DETAILED DESCRIPTION OF THE INVENTION

5.1. Definition

The term "antigen-binding protein" (ABP) refers to a protein comprising one or more antigen-binding domains that specifically bind to an antigen or epitope. In some embodiments, the antigen-binding domain binds the antigen or epitope with specificity and affinity similar to that of naturally occurring antibodies. In some embodiments, the ABP comprises an antibody. In some embodiments, the ABP consists of an antibody. In some embodiments, the ABP consists essentially of an antibody. In some embodiments, the ABP comprises an alternative scaffold. In some embodiments, the ABP consists of an alternative scaffold. In some embodiments, the ABP consists essentially of an alternative scaffold. In some embodiments, the ABP comprises an antibody fragment. In some embodiments, the ABP consists of an antibody fragment. In some embodiments, the ABP is a scFv. In some embodiments, the ABP consists essentially of an antibody fragment. For example, "anti-CD3 ABP," or "CD3-specific ABP" is an ABP, as provided herein, which specifically binds to an antigen of CD3.

The term "single-chain Fv" or "sFv" or "scFv" antibody fragments as used herein refers to a polypeptide comprising a $V_H$ domain and a $V_L$ domain in a single polypeptide chain. The $V_H$ and $V_L$ are generally linked by a peptide linker. See Plückthun A. (1994). In some embodiments, the linker is a (GGGGS)n. In some embodiments, n=1, 2, 3, 4, 5, or 6. See Antibodies from *Escherichia coli*. In Rosenberg M. & Moore G. P. (Eds.), The Pharmacology of Monoclonal Antibodies vol. 113 (pp. 269-315). Springer-Verlag, New York, incorporated by reference in its entirety.

With regard to the binding of an ABP or scFv to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the ABP to the target molecule is competitively inhibited by the control molecule.

5.2. Other Interpretational Convention

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof

5.3. Immune-Bridge Protein

The present disclosure provides an immune-bridge protein that can be expressed on the cell surface and recruit and activate immune cells. For example, the immune-bridge protein can be expressed on a cancer cell and make the cancer cell to be able to activate one or more immune effector cells.

The immune-bridge protein comprises from N terminus to C terminus: an antigen binding protein ("ABP") (e.g., scFv or other antibody fragment) against an immune cell marker, and a transmembrane domain. In some embodiments, the immune-bridge protein further comprises a cytoplasmic domain. In some embodiments, the immune-bridge protein further comprises a reporter domain, optionally wherein the reporter domain is a fluorescent protein. In some embodiments, the immune-bridge protein further comprises an epitope for immunostaining. In some embodiments, the immune-bridge protein further comprises a signal peptide (e.g., H7).

The ABP of the immune-bridge protein is determined based on target immune cells to be recruited and activated. The immune cells can be B cells, T cells, cytokine-induced killer cells, mast cells, NK cells, dendritic cells or macrophage cells, but not limited thereto. In some embodiments, the ABP is specific to one or more of the immune cell types.

In some embodiments, the ABP is specific to more than one type of immune cells. In some embodiments, the ABP is specific to T cells and/or NK cell.

In some embodiments, ABP is specific to a membrane protein expressed on the surface of a target immune cell. In some embodiments, ABP is specific to a cell surface protein of B cells, T cells, cytokine-induced killer cells, mast cells, NK cells, dendritic cells or macrophage cells, but not limited thereto.

In some embodiments, ABP specific to CD3 is used to activate T cells. In some embodiments, ABP specific to NKp46 is used to activate NK cells. In some embodiments, scFv is used as the ABP. For example, ABP is a scFv specific to CD3, or a scFv specific to NKp46. In some embodiments, an antibody or an antibody fragment other than scFv is used as the ABP.

In some embodiments, ABP known in the art is used. For example, a scFv of mAb against CD3 such as 2C11 (see Liao and Roffler, Gene Ther. 2000; De Jonge et al., Mol. Immunol. 1995), OKT3 (see Norman Ther Drug Monit 1995), or a scFv of a mAb against NKp46 such as 29A1.4 (available from ThermoFisher Scientific) and VIV-KM1 (available from Invitrogen) is used for the immune-bridge protein.

The immune-bridge protein further comprises a transmembrane domain. The transmembrane domain can be a transmembrane portion of a transmembrane protein. In some embodiments, the transmembrane domain of mouse B7 is used. In some embodiments, the transmembrane domain has the sequence of SEQ ID NO: 1 (amino acid 249-271 of NP_001346827.1). In some embodiments, the transmembrane domain has at least 80%, at least 85%, at least 90%, at least 95%, at least 97%, at least 98%, or at least 99% sequence identity to SEQ ID NO: 1.

In some embodiments, the immune-bridge protein further comprises a cytoplasmic domain. In some embodiments, the cytoplasmic domain is a cytoplasmic portion of a membrane protein. In some embodiments, the cytoplasmic domain of B7 is used. In some embodiments, the cytoplasmic domain has the sequence of SEQ ID NO: 2 (amino acid 272-306 of NP_001346827.1). In some embodiments, the cytoplasmic domain has at least 80%, at least 85%, at least 90%, at least 95%, at least 97%, at least 98%, or at least 99% sequence identity to SEQ ID NO: 2.

In some embodiments, the immune-bridge protein further comprises a reporter protein for detection of expression of the immune-bridge protein. In some embodiments, the reporter protein is a fluorescent protein. In some embodiments, the fluorescent protein is GFP.

In some embodiments, the immune-bridge protein further comprises γ1 domain sequence (hinge-$CH_2$—$CH_3$ region) of human $IgG_1$. In some embodiments, the γ1 domain induces dimerization of the immune-bridge protein. In some embodiments, the γ1 domain induces dimerization of scFvs. In some embodiments, the immune-bridge protein comprises a domain other than the γ1 domain that can induce dimerization of the immune-bridge protein.

In some embodiments the immune-bridge protein is devoid of the he γ1 domain. In some embodiments, the immune-bridge protein is devoid of a domain that induces dimerization of the immune-bridge protein.

In some embodiments, the immune-bridge protein further comprises a signal peptide. In some embodiments, the signal peptide is an H7 signal peptide. In some embodiments, the signal peptide is involved in targeting and folding of the immune-bridge protein. A signal peptide of a protein other than H7 that can help targeting and/or folding of the immune-bridge protein can be used.

In some embodiments, the immune-bridge protein further comprises an epitope for immunostaining or purification of the immune-bridge protein. In some embodiments, the epitope is in the intracellular, extracellular portion of the immune-bridge protein, or both. In some embodiments, the epitope is an HA epitope or V5 epitope.

In another aspect, the present disclosure provides a polynucleotide (immune-bridge polynucleotide) encoding the immune-bridge protein provided herein or a portion thereof. In some embodiments, the polynucleotide is codon optimized for expression in a eukaryotic cell. In some embodiments, the polynucleotide is codon optimized for expression in a mammalian cell. In some embodiment, the polynucleotide is operably linked to a regulatory region that induces or regulates expression of the immune-bridge protein from the polynucleotide. In some embodiments, the polynucleotide further comprises a barcode sequence.

In yet another aspect, the present disclosure provides a vector comprising the polynucleotide encoding the immune-bridge protein provided herein. In some embodiments, the vector is a viral vector or a plasmid. In some embodiments, the vector is a lentiviral or rAAV vector. In some embodiments, the vector is an expression vector.

In some embodiments, the polynucleotide or the vector has been isolated. In some embodiments, the polynucleotide or the vector is in a cell.

In one aspect, the present disclosure provides a host cell comprising the polynucleotide or the vector. In some embodiments, the host cell can be used for replication and amplification of the polynucleotide or the vector. In some embodiments, the host cell is used for production of the polynucleotide or the vector. In some embodiments, the host cell is used for production of the immune-bridge protein.

In some embodiments, the host cell further comprises the immune-bridge protein expressed from the polynucleotide or the vector. In some embodiments, the host cell is a mammalian cell or a prokaryotic cell. In some embodiments, the host cell is a cancer cell. In some embodiments, the host cell is a cancer cell line. In some embodiments, the host cell is a primary cancer cell obtained from a cancer patient. In some embodiments, the host cell is a primary cancer cell obtained from a cancer animal model. In some embodiments, the host cell has been sorted based on its expression of the immune-bridge protein. In some embodiments, the host cell has been sorted based on activity of the immune-bridge protein expressed from the cell.

The host cell can be transiently or non-transiently transformed with one or more vectors, polynucleotides, polypeptides, nucleic acid-protein complexes, or any combination thereof. In some embodiments, the polynucleotide or the vector is stably integrated into the genome of the host cell.

In another aspect, the present disclosure provides a population of host cells, each host cell comprising the immune-bridge protein and/or the immune-bridge polynucleotide encoding the immune-bridge protein. In some embodiments the population comprises cells from multiple donors or cell lines. In some embodiments, the population comprises primary cancer cells from multiple cancer patients.

5.4. Targeting Library of Guide RNA

In another aspect, the present disclosure provides a library comprising a plurality of targeting-library constructs. Each of the targeting-library construct comprises a sequence encoding a guide RNA (gRNA-coding sequence). In some embodiments, gRNA is a single guide RNA (sgRNA). In some embodiments, the guide RNA can be double stranded.

In some embodiments, each of the targeting-library construct comprises more than one gRNA-coding sequences.

In some embodiments, the gRNA targets one or more of genomic target sites. In some embodiments, the gRNA targets one of a plurality of genomic target sites. In some embodiments, each gRNA in the library constructs binds a unique genomic target site. In some embodiments, some gRNAs in the library constructs bind an overlapping genomic target region.

In some embodiments, a gRNA comprises a guide sequence. A guide sequence is a polynucleotide sequence having sufficient complementarity with a target polynucleotide sequence to hybridize with the target sequence and direct sequence-specific binding of a complexed nucleic acid-guided nuclease to the target sequence. The degree of complementarity between a guide sequence and its corresponding target sequence, when optimally aligned using a suitable alignment algorithm, can be about or more than about 50%, 60%, 75%, 80%, 85%, 90%, 95%, 97.5%, 99%, or more. Optimal alignment can be determined with the use of any suitable algorithm for aligning sequences. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. In preferred embodiments, the guide sequence is 10-30 nucleotides long. The guide sequence can be 15-20 nucleotides in length. The guide sequence can be 15 nucleotides in length. The guide sequence can be 16 nucleotides in length. The guide sequence can be 17 nucleotides in length. The guide sequence can be 18 nucleotides in length. The guide sequence can be 19 nucleotides in length. The guide sequence can be 20 nucleotides in length.

In some embodiments, the plurality of targeting-library constructs comprises gRNA-coding sequences encoding gRNAs collectively targeting more than 10,000 sites in the human genome. In some embodiments, the plurality of targeting-library constructs comprises sgRNA-coding sequences encoding sgRNAs collectively targeting more than 5,000, 10,000, 15,000, 20,000, 50,000, 100,000, 500, 000, or 1,000,000 sites in the human genome.

In some embodiments, each targeting-library construct further comprises a barcode sequence. Each targeting-library construct can comprise a unique pair of the gRNA-coding sequence and the barcode sequence and the barcode sequence can indicate the genomic target site of the gRNA in the construct. In some embodiments, the barcode sequence comprises a synthetic, non-natural nucleotide sequence.

In some embodiments, the targeting-library construct further comprises a coding sequence of an endonuclease. The endonuclease can be compatible with the gRNA on the same construct to form a ribonucleoprotein particle (RNP) having targetable nuclease activity. In some embodiments, the gRNA and the endonuclease are from the same species. In some embodiments, the gRNA and the endonuclease are from different species. In some embodiments, the gRNA and/or the endonuclease is not naturally occurring and artificially created.

In some embodiments, the endonuclease is a clustered regularly interspaced short palindromic repeats (CRISPR) associated protein, a zinc-finger nuclease (ZFN), a transcription activator-like effector nuclease (TALEN), MAD nuclease, or a meganuclease (MN). In some embodiments, the endonuclease is CAS9.

In some embodiments, each targeting-library construct is a viral vector or a plasmid. In some embodiments, each targeting-library construct is a lentivral vector or rAAV vector.

5.5. Cancer Cells for High-Throughput Analysis

One aspect of the present disclosure provides a population of cells modified for high-throughput analysis described herein. In some embodiments, the population comprises cancer cells. The cancer cells can be a population of cancer cells, each modified to comprise an immune-bridge protein. The cancer cells can be a population of cancer cells, each modified to comprise a targeting-library construct described herein. In some embodiments, the cancer cells are modified to comprise both an immune-bridge protein and a targeting-library construct. A population of cells can collectively comprise multiple types of targeting-library constructs. In some embodiments, the population of cells can comprise multiple types of targeting-library constructs, collectively targeting more than 5,000, 10,000, 15,000, 20,000, 50,000, 100,000, 500,000, or 1,000,000 sites in the genome of the target cell. In particular embodiments, the population of cells can comprise multiple types of targeting-library constructs, collectively targeting more than 5,000, 10,000, 15,000, 20,000, 50,000, 100,000, 500,000, or 1,000,000 sites in the human genome In some embodiments, the cancer cells comprise a polynucleotide or a vector encoding the immune-bridge protein. The cancer cells comprising an immune-bridge protein can interact with and activate immune cells by binding to an immune cell marker. In some embodiments, the cancer cells can activate T cells, NK cells, B cells, or other type of immune cells. In some embodiments, the cancer cells comprising an immune-bridge protein can activate more than one cell type. For example, some cancer cells can activate both T cells and NK cells.

In some embodiments, the cancer cells are primary cancer cells. In some embodiments, the cancer cells are cancer cells obtained from a cancer patient. In some embodiments, a population of cells are cancer cells from multiple tissues of one cancer patient. In some embodiments, a population of cells are cancer cells from a tissue of one cancer patient. In some embodiments, a population of cells are cancer cells from multiple types of tumors of one cancer patient.

In some embodiments, the cancer cells are obtained from more than one cancer patients. In some embodiments, the cancer cells are from the same type of tissues from more than one cancer patients. In some embodiments, the cancer cells are same tumors from more than one cancer patients. In some embodiments, the cancer cells are multiple tumors from more than one cancer patients. In some embodiments, the cancer cells are a cancer cell line. In some embodiments, the cancer cells are solid tumor cells.

In some embodiments, the cancer cells are sarcomas or carcinomas. The cancer cells can be bladder cancer, breast cancer, cervical cancer, colon and rectal cancer, endometrial cancer, kidney cancer, lip and oral cancer, liver cancer, melanoma, mesothelioma, non-small cell lung cancer, non-melanoma skin cancer, oral cancer, ovarian cancer, pancreatic cancer, prostate cancer, sarcoma, small cell lung cancer, or thyroid cancer cells. In some embodiments, the cancer cells are blood cancer cells.

In some embodiments, a population of cells comprise barcodes. In some embodiments, the barcodes are cell type specific. In some embodiments, the barcodes are cell-line specific. In some embodiments, the barcodes are specific to each donor. In some embodiments, the barcodes are specific to each sample. In some embodiments, the barcodes are specific to each cell line. In some embodiments, the barcodes are specific to each tumor type.

In some embodiments, a population of cells comprise multiple cell lines, wherein each cell line comprises a unique cell line-specific barcode on the targeting-library construct or immune-bridge polynucleotide. In some embodiments, a population of cells comprise cells from multiple donors, wherein cells from each donor comprises a unique donor-specific barcode on the targeting-library construct or immune-bridge polynucleotide. In some embodiments, a population of cells comprise cells from multiple samples, wherein cells from each sample comprises a unique sample-specific barcode on the targeting-library construct or immune-bridge polynucleotide. In some embodiments, a population of cells comprise cells from multiple cell types, wherein cells of each cell type comprise a unique cell type-specific barcode on the targeting-library construct or immune-bridge polynucleotide.

In some embodiments, the population of cells have been transfected with one or more polynucleotide molecules or vectors encoding an immune-bridge protein or a targeting-library construct. In some embodiments, the population of cells have been transfected with one or more polynucleotide molecules or vectors encoding an immune-bridge protein and a targeting-library construct. In some embodiments, the population of cells have been transfected with a first polynucleotide molecule encoding an immune-bridge protein and a second polynucleotide molecule encoding a targeting-library construct. In some embodiments, the population of cells have been transfected with a single polynucleotide molecule encoding both an immune-bridge protein and a targeting-library construct. In some embodiments, the population of cells include stably integrated polynucleotides encoding an immune-bridge protein and/or a targeting-library construct.

In some embodiments, the cells further comprise a marker protein encoded by the targeting-library construct or the immune-bridge polynucleotide.

In some embodiments, the marker protein is luciferase or a fluorescent protein (e.g., GFP, YFP).

In some embodiments, the cells further comprise an exogenous endonuclease. In some embodiments, the endonuclease is a clustered regularly interspaced short palindromic repeats (CRISPR) associated protein, a zinc-finger nuclease (ZFN), a transcription activator-like effector nuclease (TALEN), a MAD nuclease, or a meganuclease (MN). In some embodiments, the exogenous endonuclease is compatible with the gRNA encoded by the targeting-library construct. In some embodiments, the exogenous endonuclease is CAS9.

In some embodiments, the cells comprise a polynucleotide or a vector encoding an exogenous endonuclease. The polynucleotide or the vector is a plasmid or a viral vector. In some embodiments, the polynucleotide encoding an exogenous endonuclease is integrated into the genome of the host cell. In some embodiments, the endonuclease is electroporated into the cells.

5.6. 3D Tumor Model

In another aspect, the present disclosure provides three-dimensional (3D) culture of the cells or the population of cells described herein. Various methods available in the art for 3D cell culture can be adopted and used. For example, 3D cell culture system can use a scaffold-free method such as the ultra-low attachment plate method, hanging drop method, suspension culture method, and scaffold-based technique.

In some embodiments, a suspension culture method is used. In the case, a pool of microcapsules encapsulating the cells described herein can be used in the suspension culture. The microcapsules can have a diameter between 10 µm and 10 mm, between 10 µm and 1 mm, between 50 µm and 1 mm, between 100 µm and 1 mm, between 200 µm and 500 µm, or about between 250 µm and 500 µm.

In some embodiments, each microcapsule encapsulates a subset of a population of cells described herein. Each of the microcapsules can encapsulate cells comprising the same barcode sequence. The barcode sequence can be specific to a cell line, a donor (e.g., a cancer patient), a cell type or a sample. Thus, in some embodiments, each microcapsule encapsulates cells of the same cell line, from the same donor, of the same cell type, or from the same sample, specifically barcoded. In some embodiments, each microcapsule can encapsulate cells, collectively comprising more than one barcode sequences. In some embodiments, cells encapsulated in each microcapsule are heterogenous (e.g., multiple cell lines, cells from multiple donors, cells of multiple cell types or samples).

In some embodiments, each of the microcapsules encapsulates a subset of the population of cells obtained from a same subject. In some embodiments, each of the microcapsules encapsulates a subset of the population of cells obtained from a same cancer patient. In some embodiments, each of the microcapsules encapsulates a subset of the population of cells obtained from a single cell line.

In some embodiments, each of the microcapsules encapsulates a subset of the population of cells comprising two or more different barcode sequences. In some embodiments, the two or more different barcode sequences are sequences specific to a cell line or cell type-specific barcodes or donor specific barcodes.

In some embodiments, each of the microcapsules encapsulates a subset of the population of cells obtained from two or more subjects. In some embodiments, each of the microcapsules encapsulates a subset of the population of cells obtained from three, four, five, six, seven, eight, or more subjects. In some embodiments, each of the microcapsules encapsulates a subset of the population of cells obtained from two or more cancer patients. In some embodiments, each of the microcapsules encapsulates a subset of the population of cells obtained from three, four, five, six, seven, eight, or more cancer patients. In some embodiments, the population of cells are barcoded specific to their donors. In some embodiments, the population of cells are barcoded specific to the cell type or sample type.

In some embodiments, each of the microcapsules encapsulates a subset of the population of cells obtained from two or more cell lines. In some embodiments, each of the microcapsules encapsulates a subset of the population of cells obtained from three, four, five, six, seven, eight, or more cell lines. In some embodiments, the population of cells are barcoded specific to the cell line.

In some embodiments, the microcapsules further encapsulate immune cells. The immune cells can comprise T cells, NK cells, B cells, cytokine-induced killer cells, mast cells, dendritic cells, or macrophage. In some embodiments, each microcapsule encapsulates more than one immune cells, selected from the group consisting of: T cells, NK cells, B cells, cytokine-induced killer cells, mast cells, dendritic cells, or macrophage. In some embodiments, the immune cells comprise peripheral blood mononuclear cells (PBMCs).

The pool of microcapsules can be cultured in a culture medium. During culture, the culture medium can be stirred using a stirrer, rotating culture flask or other method known in the art.

In the culture, the population of cells can form a 3D tumor organoid.

In some embodiments, more than one pools of microcapsules can be cultured in the same medium. For example, the medium can be used to culture both a first pool of microcapsules encapsulating cells comprising a first immune bridge protein, and a second pool of microcapsules encapsulating cells comprising a second immune bridge protein. In other embodiments, the first pool of microcapsules encapsulate cells comprising a first targeting library and the second pool of microcapsules encapsulate cells comprising a second targeting library. In yet another embodiments, the first pool of microcapsules encapsulate cells comprising a first barcode sequence, and the second pool of microcapsules encapsulate cells comprising a second barcode sequence. In some embodiments, the first pool of microcausules encapsulate cells comprising first immune cells, and the second pool of microcapsules encapsulate second immune cells. In some embodiments, more than two (e.g., three, four, five, or more) pools of microcapsules are cultured together.

5.7. High-Throughput Analysis Methods

The present disclosure also provides high-throughput analysis methods using the immune-bridge protein, targeting-library construct, population of cells, and/or microcapsules, described herein. The analysis methods can be used for various purposes, including but not limited to identification new drugs or drug targets.

For example, the methods can be used to identify a genetic modification associated with enhancement or reduction in immune response of cancer cells. In particular, a genomic site or gene in a cancer cell that enhances or reduces cytotoxic effects of the immune cell can be identified. In other cases, a compound that can enhance or reduce the cytotoxic effects of the immune cells can be identified. In some embodiments, one or more test compounds associated with enhancement or reduction in immune response of cancer cells are identified. The target protein affected by the identified genetic modification or the identified test compound(s) can be used for treatment or prevention of cancer.

In some embodiments, the identified compound can be administered to a subject patient to modulate immune response (e.g., cytotoxicity). In some embodiments, an agent that can modulate activity of the identified genomic site or a protein encoded by the identified genomic site can be administered to a subject to modulate immune response (e.g., cytotoxicity). In some embodiments, the identified compound or the agent that can modulate activity of the identified genomic site or a protein encoded by the identified genomic site can induce reduction or elimination of cancer cells in a patient when administered. The agent can be a protein encoded by the genomic site, an activator or inhibitor of the protein encoded by the genomic site, or a polynucleotide, vector or cell comprising a sequence from the identified genomic site. In some embodiments, the agent is an antibody against the protein expressed from the genomic site. In some embodiments the agent comprises an anti-sense oligonucleotide against the transcript expressed from the genomic site. In some embodiments, the agent and the identified compound are administered in combination. In some embodiments, the agent and/or the identified compound can be administered in combination with other immune oncology therapy to a cancer patient to increase therapeutic effects of the immune oncology therapy.

High-Throughput Screening Using Immune-Bridge Protein

Most T cells recognize specific peptide antigens only when they are presented by MHC I or MHC II molecules from syngeneic target cells. Accordingly, traditional high-throughput screening methods requires 1) specific transgenic mouse models which produce T cells recognizing specific antigens (ex. OVA: Ovalbumin or HA: Haemagglutinin) and 2) cancer models derived from the syngeneic mouse models. This severely limits the choice of cancer models and scalability of such screening process.

Cancer cells expressing an immune-bridge protein can recruit/activate immune cells from any allogeneic sources. With the immune-bridge system, high-throughput screens of immune modulators can be performed in allogeneic cancer models with various immune cells.

For example, cancer cells expressing an immune-bridge protein are cultured with immune cells and response of the cancer cells to the immune cells can be determined. In some embodiments, cytotoxic effects are determined. Cancer cells' response to a particular type of immune cells (e.g., T cells, NK cells, dendritic cells, macrophage, peripheral blood mononuclear cells) or a combination thereof can be determined. Cancer cells that are responsive or non-responsive to the immune cells can be selected or isolated. For example, cancer cells sensitive to the immune cells are eliminated, and cancer cells less sensitive to the immune cells are enriched. Enrichment and disenrichment of certain cancer cells can be determined by sequencing a polynucleotide (e.g., genomic DNA, RNA, barcode sequence) of the cells obtained from the culture. In some embodiments, the characterization involves sequencing a barcode sequence of the cells obtained from the culture. In some embodiments, the characterization involves sequencing and identification of genotypic properties.

In some embodiments, cancer cells expressing an immune-bridge protein is further modified to express a reporter gene. In some embodiments, the reporter gene is a fluorescent protein. In some embodiments, the reporter gene is luciferase. The reporter gene can be encoded by the same construct as or different construct from the immune-bridge protein.

In some embodiments, immune response of cancer cells expressing an immune-bridge protein is tested in the presence of one or more test compounds. The method can be used to identify a test compound or a combination thereof that can alter the immune response. For example, compounds that can enhance cytotoxic effect of immune cells against cancer cells can be identified. In some embodiments, cancer cells that are particularly responsive to one or more test compounds can be identified and characterized. The term, test compounds, are used herein, refer to a small molecule (e.g., organic or inorganic compound, natural or artificial compound) or a biologic (e.g., vaccine, cell, blood, blood component, allergen, gene, tissue, or protein).

In some embodiments, the immune response is tested in a 3D tumor model. In some embodiments, cancer cells expressing an immune-bridge protein and immune cells are encapsulated together in a microcapsule. In some embodiments, a pool of microcapsules, each encapsulating both cancer cells expressing an immune-bridge protein and immune cells are cultured together in a culture medium. In some embodiments, the pool of microcapsules collectively encapsulates multiple types of cancer cells (e.g., multiple cell lines, cancer types, cells from multiple donors, etc.). In some embodiments, cancer cells in the microcapsules are barcoded specific to the cell sample, type, donor, etc. In some embodiments, the pool of microcapsules collectively encapsulates multiple types of immune cells (T cells, NK cells, dendritic cells, macrophage, and/or PBMCs).

In some embodiments, the pool of microcapsules is cultured in the same culture medium and the one or more test compounds are applied to the culture medium. When multiple test compounds are tested, they can be applied individually, serially or in combination.

Accordingly, the method provided herein can comprise the steps of culturing a population of cancer cells or incubating a pool of microcapsules, and analyzing cells obtained from the culture. In some cases, the population of cancer cells are cultured in the presence of immune cells. In some embodiments, the step of analyzing comprises sequencing a polynucleotide of cells obtained from the culture. The sequencing can provide information related to the identity of the cells. The polynucleotide can be a barcode sequence or endogenous (e.g., genomic sequence or mRNA sequence) sequence of the cells.

When multiple barcodes specific to various cancer cell samples are used, barcodes of cancer cells under the no drug and drug conditions can be sequenced and compared understand cell types existing under the two different conditions. In some embodiments, the ratio of barcodes, representing various tumor samples, is calculated to understand the drug response across the multiple tumor samples.

In some embodiments, cancer cells expressing an immune-bridge protein and optionally with a reporter protein are cultured in multi-well plates in the presence of immune cells. Subsequently, test compounds are individually applied to each well. The growth and/or other physical or biological properties of the cells treated or not treated with the test compounds are determined and compared. In some embodiments, the growth and/or other physical or biological properties of the cells cultured in the presence or absence of the immune cells are determined and compared.

In some embodiments, test compounds that enhance cytotoxicity against cancer cells in the presence of immune cells are identified. In some embodiments, test compounds having cytotoxic effects against cancer cells in the absence of immune cells are identified. In some embodiments, test compounds that enhance cytotoxicity against cancer cells in the presence, but not in the absence of, the immune cells are selected. In some embodiments, test compounds that enhance cytotoxicity against cancer cells in the absence, but not in the presence of, the immune cells are selected. In some embodiments, test compounds that enhance cytotoxicity against cancer cells by only a particular type of immune cells are selected. In some embodiments, test compounds that enhance cytotoxicity against cancer cells by several types of immune cells are selected.

High-Throughput Endonuclease (e.g., CRISPR) Screening

The analysis system described herein can be used to analyze cancer cells genetically modified using a targeting library of guide RNA and an exogenous endonuclease described herein. Changes of immune response of the cancer cells or changes of growth rates of the cancer cells unrelated to immune response resulting from the genetic modification can be analyzed using the analysis system provided herein. A new drug or drug target can be identified by analyzing the relation between the genetic modification and the changes in the immune response or the changes in the cancer intrinsic growth rates.

In some embodiments, the method comprises the steps of obtaining cancer cells modified to comprise an exogenous endonuclease, and a targeting library comprising targeting-library constructs and incubating the cancer cells in a condition for genetic modification (e.g., knockout) by the endonuclease and the target library. In some embodiments, the cancer cells are further modified to comprise a barcode sequence. The modified cancer cells are cultured in a 3D tumor model described herein (e.g., for at least one, two, three, four, or five weeks). Enrichment and dis-enrichment of certain cancer cells after the culture can be measured by sequencing counts of gRNAs, barcodes, or other sequences specific to the cancer cells. From the analysis, genetic modifications associated with cancer cell growth can be identified.

In some embodiments, the method comprises the steps of obtaining cancer cells modified to comprise an exogenous endonuclease, and a targeting library comprising targeting-library constructs and incubating the cancer cells in a condition for genetic modification (e.g., knockout) by the endonuclease and the target library. In some embodiments, the cancer cells are further modified to comprise a barcode sequence. The modified cancer cells are divided into two groups and one group is cultured in the presence of one or more test drugs and the other group is cultured in the absence of the one or more test drugs. The cancer cells can be cultured in a 3D tumor model described herein (e.g., for at least one, two, three, four, or five weeks). Enrichment and dis-enrichment of certain cancer cells after the culture can be measured by sequencing counts of gRNAs, barcodes, or other sequences specific to the cancer cells. From the analysis, genetic modifications associated with cancer cell growth and response to the one or more test drugs can be identified.

In some embodiments, the method comprises the steps of obtaining cancer cells modified to comprise an immune-bridge protein, an exogenous endonuclease, and a targeting library comprising targeting-library constructs and incubating the cancer cells in a condition for genetic modification (e.g., knockout) by the endonuclease and the target library. In other embodiments, the method comprises the steps of obtaining cancer cells modified to comprise an exogenous endonuclease and a targeting library comprising targeting-library constructs, incubating the cancer cells in a condition for genetic modification (e.g., knockout) by the endonuclease and the target library, and introducing an immune-bridge protein or a polynucleotide encoding the immune-bridge protein to the modified cancer cells.

In some embodiments, more than one targeting libraries of gRNA are used. Each of the multiple libraries can be uniquely barcoded. The barcoded targeting libraries can be separately introduced into multiple tumor samples. The tumor samples can be encapsulated into microcapsules, multiplexed and cultured for a given screening period. At the end of the screening, genomic DNAs of the tumor cells can be extracted and sgRNAs and/or associated barcodes can be sequenced. gRNA counts can be demultiplexed by the barcodes or the gRNA coding sequence unique to each tumor sample and the gRNA counts traced back to the original tumor samples are used to determine phenotypic effects of mutation by the gRNA in each tumor sample.

In a particular embodiment, two cancer samples (Sample1 and Sample2) are separately transduced with a targeting library of gRNA uniquely barcoded (BC1 and BC2). The cancer samples can be tested individually (non-mixed sample) or in a mixture (mixed sample). gRNA can be counted from a non-mixed sample without demultiplexing. But gRNA from mixed samples need to be demultiplexed. In some embodiments, gRNAs from the mixed sample are demultiplexed by barcodes. The gRNAs can be counted for each tumor sample.

The method involving multiplexing and demultiplexing steps enable two genome-scale screening to be performed simultaneously in two, multiplexed tumor samples. In some embodiments, three, four, five, or more genome-scale screening can be performed simultaneously.

The genetically modified cancer cells can be incubated with immune cells (e.g., T cell, NK cells or other immune cells) in a condition where the immune cells can interact the cancer cells. With one or multiple pulses of treatment with the immune cells, knock-out clones that render cancer cells more sensitive to the immune cells are more significantly reduced or eliminated, and clones that render cancer cells more resistant to the immune cells are enriched. Enrichment and dis-enrichment of such cancer cells can be measured by sequencing counts of gRNAs, barcodes, or other sequences specific to the cancer cells. In particular, the sequencing counts of gRNAs, barcodes or other specific sequences can be compared between cancer cells treated with immune cells and cancer cells untreated with immune cells. The counts of gRNAs, barcodes, or the specific sequences can be used to characterize genetic modifications in the cancer cells, for example, identity and location of mutation and its effects.

Results from the analysis can be used to determine phenotypic effects of various genetic modification, particularly effects on response to immune cells and/or on intrinsic tumor growth rates.

In some embodiments, one or more test compounds are applied to the culture of the genetically modified cancer cells and the immune cells (e.g., T cell or NK cells). After application of the one or more test compounds, enrichment and dis-enrichment of certain cancer cells can be measured by sequencing counts of gRNAs, barcodes or other specific sequences in the cancer cells. Comparison of the sequencing counts of gRNAs, barcodes or other specific sequences between cancer cells treated with the one or more test compounds and cancer cells not treated with the one or more test compounds in the presence or the absence of immune cells can be used to determine phenotypic effects of various genetic modification and/or the test compounds on the immune response.

In some embodiments, the cancer cells and the immune cells are incubated in a 3D tumor model. In some embodiments, the cancer cells and the immune cells are incubated in microcapsules. In some embodiments, gRNAs are cloned in constructs further comprising barcodes. The measurement of sequencing counts of gRNAs in cancer cells can be performed by sequencing the barcode sequences.

In one exemplary embodiment, Cas9 expressing cancer cells are transduced with a construct encoding an immune-bridge protein. A targeting library of lentivirus encoding sgRNAs targeting 20,000 human genes is then transduced into the cancer cells. This creates a pool of 20,000 knock-out cancer cells expressing the immune-bridge protein. T cells or NK cells are prepared from PBMCs and applied to the cancer cells. With multiple pulses of immune cell treatments, knock-out clones that render cancer cells resistant to the immune cells are enriched, whereas knock-out clones that render cancer cells more sensitive to the immune cells are dis-enriched. Enrichment and dis-enrichment of such knock-out clones are measured by comparing deep-sequencing counts of sgRNAs in the immune cell treated cancer cells to those of sgRNAs in the untreated cancer cells.

High-Throughput Screening of Autoimmune Disease Drug Candidates

High-throughput screening methods and systems disclosed herein can be also used to analyze non-cancer cells. For example, they can be used to identify a new drug or drug target for treatment of autoimmune disease.

In some embodiments, cells obtained from an autoimmune disease patient are modified to express the immune-bridge protein and plated in multi-well plates. A library of test compounds can be tested with the cells in the presence or absence of immune cells. For example, the test compounds can be applied to the multi-well plates containing the cells expressing an immune-bridge protein with or without immune cells.

Cell growth and other physical or biological properties can be measured and compared between the cells in various conditions, e.g., cells treated with drug compounds in the presence of immune cells and in the absence of immune cells, or cells treated with drug compounds and cells not treated with drug compounds. From the comparison, test compounds that are involved in modulation of the interaction between the cells and immune cells are identified. In some embodiments, test compounds that reduce or eliminate abnormal immune response are identified.

Test compounds identified using the method described herein can be used to treat an autoimmune disease.

5.8. Kits

In one aspect, the present disclosure provides a kit for the high-throughput analysis and method provided herein.

The kit can comprise the immune-bridge protein or the immune-bridge polynucleotide or vector that encodes the immune-bridge protein. In some embodiments, the immune-bridge polynucleotide or vector is an expression vector that can be transfected into a target cell and induce expression of the immune-bridge protein.

In some embodiments, the kit comprises a cell comprising the immune-bridge protein or the immune-bridge polynucleotide or vector. In some embodiments, the polynucleotide encoding the immune-bridge protein is stably integrated into the genome of the cell.

In some embodiments, the kit comprises a targeting library of guide RNA. In some embodiments, the targeting library comprises gRNA coding sequences. The gRNAs in a library can collectively target more than 15,000 sites, 20,000 sites, 50,000 sites, 100,000 sites or more. In some embodiments, the targeting library comprises expression vector comprising gRNA coding sequences. In some embodiments, the expression vector further comprises barcode sequences.

In some embodiments, the kit comprises an exogenous nuclease or a polynucleotide encoding an exogenous nuclease. In some embodiments, the exonuclease is selected from the group consisting of a clustered regularly interspaced short palindromic repeats (CRISPR) associated protein, a zinc-finger nuclease (ZFN), a transcription activator-like effector nuclease (TALEN), MAD nuclease, and a meganuclease (MN). In some embodiments, the exogenous nuclease is CAS9.

In some embodiments, the kit further comprises a polynucleotide encoding a marker protein. In some embodiments, the marker protein is luciferase or other reporter protein.

In some embodiments, the nuclease polynucleotide or the marker polynucleotide is in a viral vector, optionally a lentiviral vector.

In some embodiments, the kit further comprises one or more barcode sequences.

6. EXAMPLES

6.1. Example 1: Design and Application of Immune-Bridge Proteins

Figure 1:
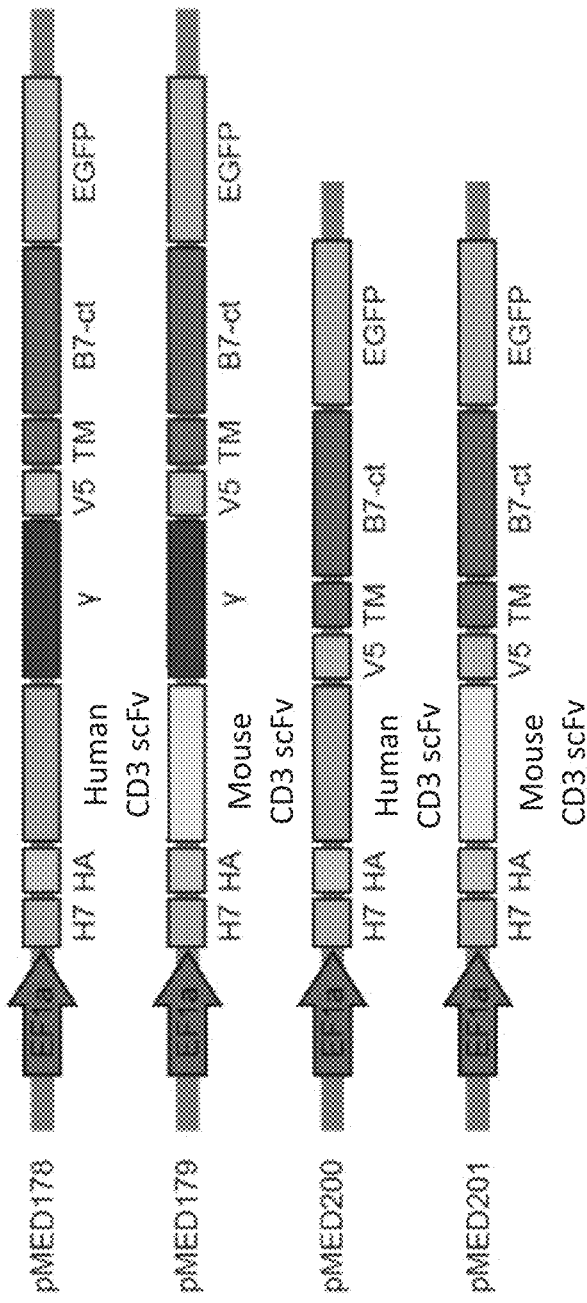

Several immune-bridge proteins were designed and generated as illustrated in FIG. 1 to develop a high-throughput screening system. The immune-bridge protein contains a scFv specific to an immune cell marker (e.g., CD3, NKp46). The polynucleotide encoding the recombinant protein was cloned in the lentiviral vector and transduced into cancer cells for stable membrane expression of the scFv.

When the recombinant membrane proteins were expressed on cancer cells, they could recruit/activate immune cells from any allogeneic sources.

As examples, construct designs for pMED178, pMED179, pMED200 and pMED201, are provided in FIG. 1. The constructs include H7 signal peptide; γ1 domain sequence (hinge-$CH_2$—$CH_3$ region) of human $IgG_1$ to induce dimerization of scFv for pMED178 and pMED200; V5 epitope for immunostaining; transmembrane domain of B7 (B lymphocyte activation antigen); cytoplasmic domain of B7 (B7-ct) to achieve high-expression of scFV; and EGFP fluorescent marker. The proteins further include one of two scFvs—scFV against mouse CD3 for pMED179 and pMED201 to activate mouse T cells and scFV against human CD3 for pMED178 and pMED200 to activate human T cells. scFvs targeting a different immune cell marker can be used to recruit/activate the same or different types of immune effector cells with varying activation signals.

As illustrated in FIG. 1, pMED178 construct comprises EF1a promoter followed by a coding sequence of pMED178 immune-bridge protein comprising: H7 signal peptide, HA epitope, human CD3scFv, γ1 domain sequence (hinge-$CH_2$—$CH_3$ region) of human $IgG_1$, V5 epitope, a transmembrane domain, a cytoplasmic domain of B7 and a reporter protein (EGFP).

pMED179 construct comprises EF1a promoter followed by a coding sequence of pMED179 immune-bridge protein comprising: H7 signal peptide, HA epitope, mouse CD3scFv, γ1 domain sequence (hinge-$CH_2$—$CH_3$ region) of human $IgG_1$, V5 epitope, a transmembrane domain, a cytoplasmic domain of B7 and a reporter protein (EGFP).

pMED200 construct comprises EF1a promoter followed by a coding sequence of pMED200 immune-bridge protein comprising: H7 signal peptide, HA epitope, human CD3scFv, V5 epitope, a transmembrane domain, a cytoplasmic domain of B7 and a reporter protein (EGFP).

pMED201 construct comprises EF1a promoter followed by a coding sequence of pMED201 immune-bridge protein comprising: H7 signal peptide, HA epitope, mouse CD3scFv, V5 epitope, a transmembrane domain, a cytoplasmic domain of B7 and a reporter protein (EGFP).

The pMED178 and pMED200 constructs were transfected to cancer cells to test capability of the immune-bridge proteins to induce selective killing by T cells. MDA-MB-231 cells (triple negative breast cancer model) were transduced with a construct encoding 1) GFP control, 2) pMED178 immune-bridge (dimeric human CD3 scFV), or 3) pMED200 immune-bridge (monomeric human CD3 scFV). The transfected MDA-MB-231 cancer cells were treated with human naive T cells and the growth of MDA-MB-231 cells were measured. The relative growth of immune-bridge cells compared to control GFP cells were plotted over 120 hours post initial T cell treatment and provided in FIG. 6A. The data show selective decrease of pMED178 and pMED200 cancer cells in response to T cells.

The selective killing of immune-bridge cells by T cells were further confirmed in a separate set of experiment. Specifically, various cancer cell lines (H460, A549, RKO, SK-HEP1, HCC1806, HEP3B, and KNS81) were transfected with one of the immune-bridge constructs (pMED178, pMED179, pMED200 and pMED201) and cultured as 3D spheroids (tumors). Human PBMCs (hPBMCs) were added to the cancer cells and tumor mass was monitored by GFP signals of the immune-bridge proteins using Incucyte S3 (Sartorius), a live-cell time-lapse microscopy system. Relative tumor mass between PBMC+ and PBMC− samples was calculated and plotted in FIG. 12. over time after PBMCs were added. pMED200 consistently induced substantial tumor cell death whereas pMED178 was inconsistent. pMED179 and pMED201 (negative controls) dd not induce significant tumor cell death with human PBMCs.

Activation of T cells was also measured in each condition using CD69, an early T cell activation marker. The results are provided in FIG. 6B. They show that immune-bridge proteins on the pMED178 and pMED200 cancer cells can activate naive T cells in PBMC.

Cancer cells transfected with the immune-bridge proteins could also induce expansion of human CD8+ and CD4+ T cells in naïve human PBMC as provided in FIG. 11A. Percentage of CD3+/CD8+ and CD3+/CD4+ cells in PBMCs exposed to cancer cells with indicated immune-bridge proteins were measured by cell analyzer (Bio-Rad ZE5). pMED200 was particularly effective, and induced expansion of human CD8+ and CD4+ T cells at a statistically significant level.

Cancer cells transfected with pMED200 were also tested for activation of T cells using CD25, a T cell activation marker. FIG. 11B shows increase of human CD8+ and CD4+ T cells in naïve human PBMC after exposure to cancer cells expressing pMED200.

pMED179 and pMED201 didn't show activation on T cells. The results were expected because pMED179 and pMED201 work only on mouse T cells since they bind only to mouse CD3, but not to human CD3. Cancer cells expressing pMED178 demonstrated significantly lower activation of T cells compared to pMED200. Without wishing to be bound by a theory, it is believed that the lower activity on T cells is associated with Gamma domain (γ) in pMED178 that induced excessive aggregations of the immune-bridge protein, which led to cytotoxicity to the cells expressing pMED178. pMED200 shows much weaker oligomerizations, which seem to enhance T-cell activations exposed to it without excessive aggregations and toxicities.

Figure 3:
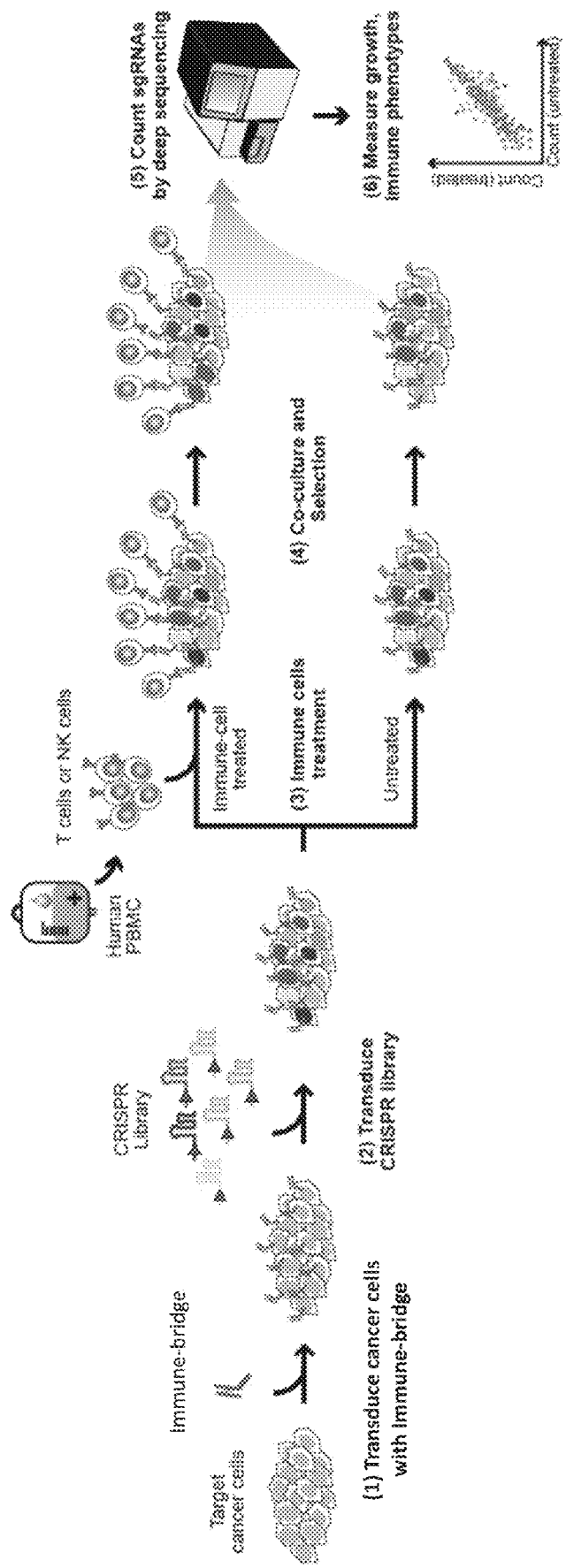
FIG. 3 illustrates a high throughput CRISPR screening procedure using immune-bridge proteins as described in Example 2.

6.2. Example 2: High Throughput CRISPR Screening System for Identifying Immune-Oncology Targets MDA-MB-231 cancer cells were modified to express Cas9 and the immune-bridge protein. The cells were further modified to contain a pool of sgRNA lentivirus targeting 20,000 human genes. These modifications provided a library of 20,000 knock-out cancer cells expressing the immune-bridge protein on the membrane. (See FIGS. 3(1) and (2)).

Figure 2A:
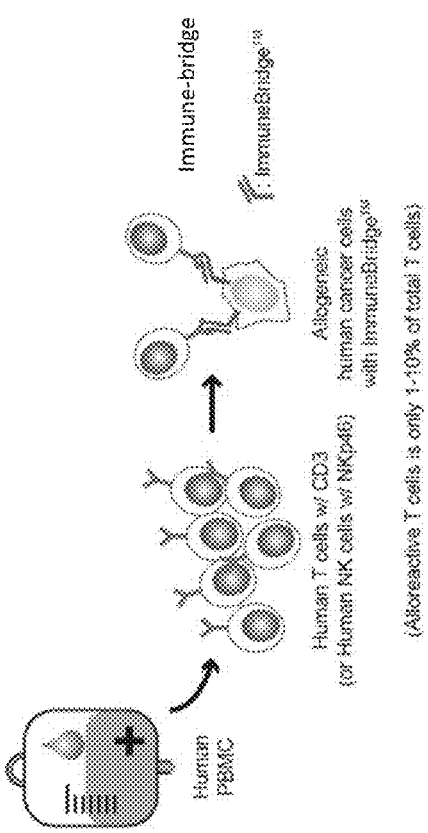
Figure 2B:
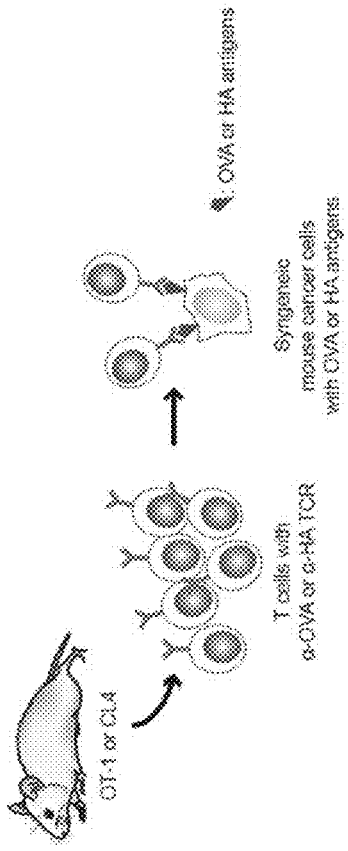

T cells (or NK cells) were prepared from PBMCs and applied to the knock-out cancer cells expressing the immune-bridge protein. (See FIG. 2B and FIG. 3(3)) With multiple pulses of immune cell treatments, knock-out cancer cells resistant to the immune cells were enriched, whereas knock-out clones sensitive to the immune cells were dis-enriched. Knock-out clones enriched or dis-enriched by the immune cell treatment were determined by comparing deep-sequencing counts of sgRNAs in the cancer cell library treated with the immune cells and those not treated with the immune cells. (See FIGS. 3(5) and (6)). From the experiment, immune-oncology drug targets were identified (see FIG. 7). A negative immune effect means that deletion of the gene makes the MDA-MB-231 cancer cells more vulnerable to immune cell attack whereas a positive immune effect means deletion of the gene makes the cancer cells more resistant to immune cells.

A volcano plot of genome-scale CRISPR screening data is provided in FIG. 7. It identifies several targets (e.g., PTPN2, IRF1, RELA, PD-L1), including PD-L1, a well-known immune suppressor expressed in MDA-MB-231 cells and therefore predicted to have a strong negative immune effect. PD-L1 was indeed identified as one of top hits with negative immune effects. PTPN2, IRF1, and RELA are also known immune regulators and they were also identified as top hits. These demonstrate that the high-throughput analysis method provided herein is an effective way to identify novel drugs and drug targets.

6.3. Example 3: Use of Immune-Bridge Proteins for Identification and Validation of Immune-Oncology Targets Wild type and PD-L1 KO triple negative breast cancer (TNBC) cell lines were transfected with the pMED200 construct to express pMED200 immune-bridge protein. The wild type and PD-L1 KO cells expressing pMED200 were cultured and exposed to three different PBMC combinations (PBMC #1, #2, and #1+2). Tumor mass in the cultures was monitored over time in Incucyte S3 by GFP marker expressed in the tumors and the relative tumor mass (PBMC+/PBMC−) was calculated and plotted in FIG. 13. The results show that PD-L1 KO tumor cells expressing pMED200 are significantly more sensitive to PBMC compared to WO tumor cells expressing pMED200. This tumor-immune co-culture functional assay shows that pMED200 can be used to recapitulate specific interactions between human immune cells and tumor cells with various genetic contexts and can be used to identify novel immune-oncology targets.

The functional tumor-immune co-culture assays were performed on additional immune-oncology targets (PTPN2 and MEDIC_001) identified from experiments described in Example 2. Wild type and PD-L1, PTPN2 or MEDIC_001 KO triple negative breast cancer (TNBC) cell lines were transfected with the pMED200 construct and seeded in agarose gel with and without hPBMCs. The tumor growths were monitored by GFP signals in tumors in the Leica Thunder Microscopy and the images are provided in FIGS. 14A and 15A. The relative tumor mass between PBCM+ and PBMC− samples was measured across wild type, PD-L1 KO, MEDIC_001 KO, and PTPN2 KO TNBC #1 tumors and provided in FIGS. 14B and 15B. The results show that PD-L1, PTPN2 KO as well as MEDIC_001 KO were significantly more sensitive by showing greater tumor reductions by hPBMCs than the wild type.

Figure 4:
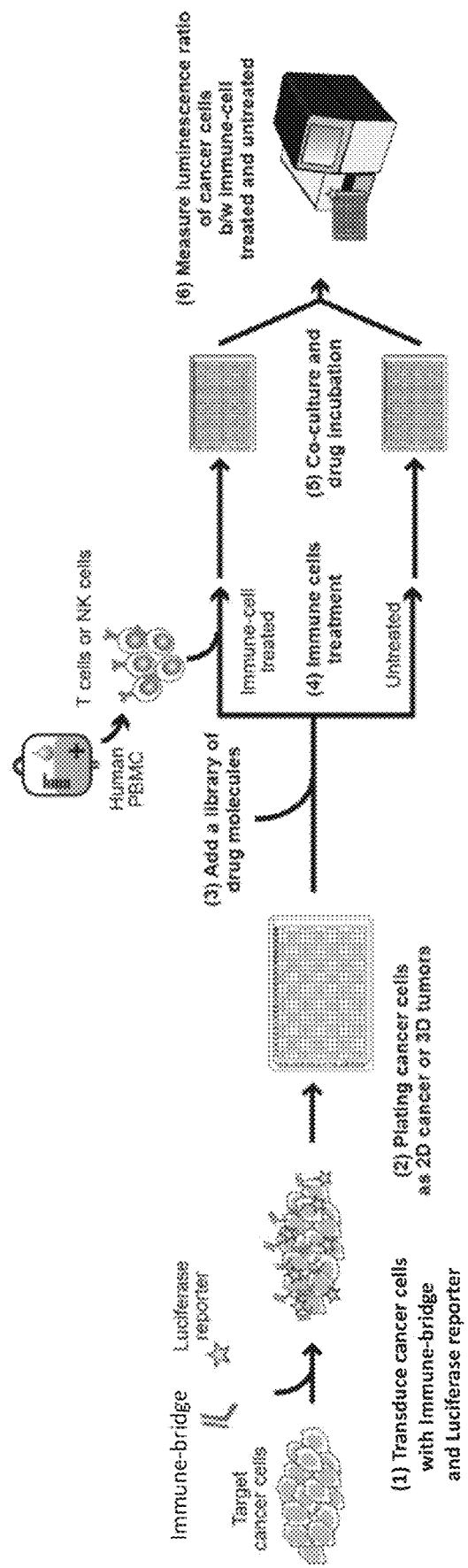
FIG. 4 illustrates a high throughput drug screening system using immune-bridge proteins as described in Example 4.

6.4. Example 4: High Throughput Drug Compound Screening for Immuno-Oncology Drug Candidates or Autoimmune Disease Drug Candidates Cancer cells were modified to express the immune-bridge protein and luciferase and plated in multi-well plates. (See FIG. 4) The cancer cells were treated with a library of drug compounds in the presence or absence of immune cells. Cell growth was measured and compared between cancer cells treated with drug compounds in the presence of immune cells and in the absence of immune cells. From the comparison, drug compounds that modulate the interaction between cancer cells and immune cells are identified.

A similar experiment is performed with non-cancer cells modified to comprise the immune-bridge protein and luciferase. The cells are plated in multi-well plates and treated with a library of drug compounds in the presence or absence of immune cells. Cell growth and other physical or biological properties are measured and compared between cells treated with drug compounds in the presence of immune cells and in the absence of immune cells. From the comparison, drug compounds that are involved in abnormal cytotoxic effects of the immune cells against the modified cells are identified. The identified drug compounds can be used for treatment of autoimmune diseases.

6.5. Example 5: Generation of 3D Tumor Models 3D tumor models were generated by encapsulating tumor samples into microcapsules. The microcapsules were generated as described below.

Oxidating alginate: Sodium alginate was processed as has been described previously. Briefly, 2 g of alginate was dissolved in 100 ml of distilled water. Different amounts of sodium periodate were added in the alginate solution to modulate the percentage of alginate oxidation and the reaction proceeded for 17 h under constant stirring in dark room. The different amounts of ethylene glycol were added and stirred in the solution for 30 mins at room temperature. The resulting solution was dialyzed in deionized water for three days (molecular weight cutoff of 10 kDa). The product was then sterile filtered, frozen and lyophilized.

Solutions and Cell Suspension Preparation: The outer solution was prepared by dissolving 2% wt/vol sodium alginate in autoclaved DI water and by adding 0.5 mM SDS surfactant. The solution was sterilized and stored at 4° C. The oxidized alginate (3% wt/vol) was dissolved in growth medium and mixed with the type A gelatin solution. Cells were detached using an enzyme-free cell dissociation buffer (Accutase) and resuspended in serum-free DMEM at a final concentration of 30 million cells/ml. The inner solution (IS) was prepared by mixing the cell solution with the alginate-gelatin (or Matrigel™) mixture or any alternative hydrogel matrix materials such as PEG.

Encapsulation procedure and characterization of encapsulation efficiency: Microcapsule production was performed with the electrical acoustic micro jetting system (Bushi, Encapsulator). Two of the solution (outer solution and inner solution) were prepared to produce microcapsule and were transferred into each pressure bottle. Both outer solution and inner solution were pushed by air pressure into the microcapsule producing unit including the co-centric nozzle system. The liquid flow rate and the vibration frequency were respectively modulated to make a clear microcapsule chain. The liquid jet of microcapsule chain was transformed into a funnel-like multi-line stream by activating the electrostatic dispersion unit. The separated capsules under the electrostatic charge were solidified by entering into the hardening solution containing 100 mM calcium chloride and traces of Tween 20 surfactant. Microcapsules were immediately sieved with 200 µm Cell Strainers, washed in 300 mM D-sorbitol solution and transferred to the appropriate culture medium within less than 15 min. After use, the micro fluidic device was cleaned with disinfectant, 70% ethanol and deionized water. The encapsulation efficiency is evaluated from image analysis of hundreds of capsules taken under the microscope. The microcapsules containing cells are produced at a rate around 500 capsules per second and collected for a couple of minutes.

6.6. Example 6: Drug Tests in Multiplexed 3D Tumor Models

Figure 5:
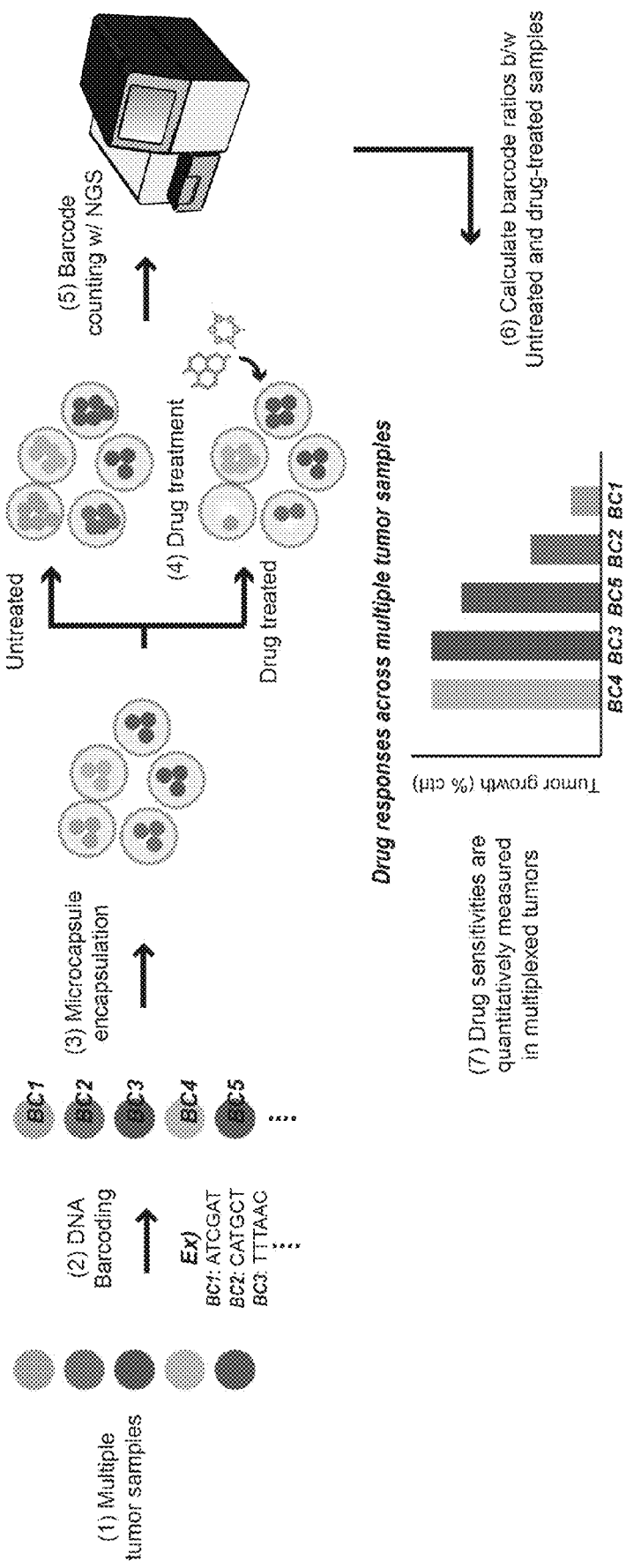
FIG. 5 illustrates a high throughput drug screening system using multiplexed 3D tumor models as described in Example 6.

Multiple tumor samples were transduced with lentivirus vectors containing DNA barcodes unique to each tumor sample. (FIG. 5(1)) The unique barcodes are represented as "BC1," "BC2," "BC3," etc. in FIG. 5.

The barcoded, multiple tumor samples were then encapsulated into microcapsules whose size ranged between 100 µm and 1 mm, as described above in Example 5. The outer layer of the microcapsule was a hard/non-flexible alginate based shell, whereas the inner layer was a degradable, flexible hydrogel to allow anchorage-independent 3D growth of tumor cells inside. For example, Matrigels, degradable alginate hydrogels, degradable PEG, and any other hydrogel polymers can be used for 3D culture of cells. Microcapsules containing multiple tumor samples were then cultured in the presence or absence of a test drug. After the reaction, tumor cells were extracted from microcapsules and their genomic DNAs were prepared from the tumor cells for barcode analysis. (FIGS. 5(5) and 5(6)) The ratio of barcodes between the no drug and drug conditions were calculated to understand the drug response across the multiple tumor samples. Multiplexing of DNA barcoded cancer samples have been previously tried for drug tests (Yu et al., 2016), but they are mainly limited to in vitro 2D cancer models (or mouse models) with different readouts (PRISM detection). The method described herein is novel in that it combines traditional cell DNA barcoding methods with micro-capsule encapsulation techniques to allow drug tests in multiplexed 3D tumor models without crosstalk between tumors, which allows significant reduction of time and cost for performing such drug screens in 3D tumors compared to the more traditional ways based on multi-well plates.

6.7. Example 7: Multiplexed CRISPR Functional Genomics in 3D Tumor Model

A schematic of multiplexed CRISPR functional genomics in 3D tumor models is provided in FIG. 8. One genome-scale CRISPR library contains hundreds of thousands of sgRNAs targeting 20,000 human genes. Multiple sets of genome-scale CRISPR libraries were individually barcoded with a DNA sequence unique to each tumor sample. (e.g., BC1 and BC2 in FIG. 8. The barcoded CRISPR libraries were then separately transduced into tumor samples using a protocol disclosed in Han, K. et al. (2020) "CRISPR screens in cancer spheroids identify 3D growth-specific vulnerabilities", Nature, 580 (7801), pp. 136-141. Tumor samples were then encapsulated into microcapsules as described above in FIG. 5.

Multiple sets of tumor samples were multiplexed and cultured. After culturing for 28 days, tumor cells were extracted and genomic DNAs were prepared from the tumor samples. sgRNAs and associated DNA barcodes were read and counted by Illumina NGS using paired-end sequencing protocol, and finally sgRNA counts were demultiplexed by the DNA barcodes unique to each tumor sample. The sgRNA counts traced back to the original tumor samples were used to calculate CRISPR-induced genetic changes in each tumor sample.

As an example, demultiplexing of sgRNA counts from two mixed cancer samples is illustrated in FIG. 9A. Two cancer samples (Sample1 and Sample2) were separately transduced with genome-scale CRISPR libraries uniquely barcoded (BC1 and BC2). The two cancer samples were cultured individually (Sample 1 (non-mix) or Sample 2 (non-mix)) or combined and cultured together (Sample 1 & 2 (mix)) (See FIG. 9A)

Their genomic DNAs were extracted from two cancer samples separately (non-mix samples) or from two mixed cancer samples (mix sample). sgRNAs were counted from the non-mix samples, which didn't require demultiplexing. sgRNAs from the mixed sample were first demultiplexed by DNA barcodes and counted for each tumor sample. Pairwise correlation of sgRNA counts from Sample1 and Sample 2 in the non-mix or the mix samples were compared and their pairwise correlation values are provided as the heatmap of FIG. 9B. The heatmap clearly shows that demultiplexed sgRNA counts from the mixed sample are similar to their original counterparts in the non-mixed samples: Sample1 (non-mix) shows the high correlation (>0.95 pearson correlation) with Sample1 (mix). Sample2 (non-mix) shows the high correlation with Sample 2 (mix) as well. Samples marked with * were prepared with two-step PCRs to make sequencing library for NGS whereas all the other samples were prepared with one-step PCR.

Two genome-scale CRISPR screens were simultaneously performed in two, multiplexed tumor samples (RKO (colon tumor) and OVCAR8 (ovarian tumor) samples) following the procedure described in FIG. 8. sgRNAs were demultiplexed and counted as described above and CRISPR effects were calculated for each tumor sample from demultiplexed sgRNA counts. FIG. 10A and FIG. 10B plot the genes that affected cancer cell growth based on the growth effect of the CRISPR induced knockout (x-axis) and the confidence score (y-axis). The assay identified several genes (e.g., UBA6, YPEL5, CDK2, XRN1, SDHA, SLC7A5, PRKRA, CAD), which are known to be associated with cancer cell growth.

7. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

8. SEQUENCE LISTING

| SEQ ID NO | Sequence |
| --- | --- |
| SEQ ID NO: 1 (amino acid 249-271 of NP_001346827.1) | vl fgagfgavit vvvivviikc f |
| SEQ ID NO: 2 (amino acid 272-306 of NP_001346827.1) | ckhrscfrr neasretnns ltfgpeeala eqtvfl |

What is claimed is:

1. A population of cancer cells comprising:
   (i) an immune-bridge protein comprising from N terminus to C terminus:
   a. an scFv against an immune cell marker,
   b. a transmembrane domain,
   c. a cytoplasmic domain, and
   d. a reporter domain, optionally wherein the reporter domain is a fluorescent protein; and
   (ii) a targeting-library construct comprising a sgRNA-coding sequence encoding a sgRNA targeting one of a plurality of genomic target sites.

2. The population of cancer cells of claim 1, wherein the immune cell marker is a cell surface protein of a T cell or NK cell.

3. The population of cancer cells of claim 1, wherein the transmembrane domain is a transmembrane domain of B7 and the cytoplasmic domain is a cytoplasmic domain of B7.

4. The population of cancer cells of claim 1, wherein the immune-bridge protein further comprises (i) an epitope for immunostaining in the intracellular or extracellular portion of the immune-bridge protein, optionally wherein the epitope is selected from HA epitope and V5 epitope and (ii) a signal peptide at the N-terminal end of the immune-bridge protein, optionally an H7 signal peptide.

5. The population of cancer cells of claim 1, wherein the immune cell marker is CD3.

6. The population of cancer cells of claim 1, wherein the immune cell marker is NKp46.

7. The population of cancer cells of claim 1, wherein the immune-bridge protein further comprises a hinge-CH2-CH3 region of human IgG1 in the extracellular portion of the immune-bridge protein.

8. The population of cancer cells of claim 1, collectively comprising multiple types of targeting-library constructs targeting the plurality of genomic target sites.

* * * * *